(12) United States Patent
Chen et al.

(10) Patent No.: US 9,389,162 B2
(45) Date of Patent: Jul. 12, 2016

(54) DETECTION OF ANALYTE USING COFFEE-RING EFFECT

(71) Applicant: City University of Hong Kong, Kowloon (HK)

(72) Inventors: Ting-Hsuan Chen, Kowloon Tong (HK); Wei Liu, Kowloon Tong (HK); Yuanhang Li, Kowloon Tong (HK)

(73) Assignee: CITY UNIVERSITY OF HONG KONG, Kowloon (HK)

( * ) Notice: Subject to any disclaimer, the term of this patent is extended or adjusted under 35 U.S.C. 154(b) by 166 days.

(21) Appl. No.: 14/249,528

(22) Filed: Apr. 10, 2014

(65) Prior Publication Data

US 2015/0293011 A1  Oct. 15, 2015

(51) Int. Cl.
*G01N 33/543* (2006.01)
*G01N 33/558* (2006.01)
(Continued)

(52) U.S. Cl.
CPC ........ *G01N 15/0631* (2013.01); *G01N 15/0625* (2013.01); *G01N 33/54313* (2013.01);
(Continued)

(58) Field of Classification Search
CPC ....... G01N 19/08; G01N 33/48; G01N 33/53; G01N 33/5308; G01N 33/543; G01N 33/54313; G01N 33/545; G01N 33/547; G01N 33/551; G01N 33/558; G01N 33/68; G01N 21/8483; G01N 21/88; G01N 21/8803; G01N 21/89; G01N 21/8914; G01N 15/0625; G01N 15/0631; G01N 1/38; G01N 2001/4027; G01N 2015/0053; G01N 2015/0065; G01N 2015/0681; Y10T 436/25; Y10T 436/25375; Y10T 436/2575

USPC .......... 436/63, 73, 74, 86, 94, 164, 174, 177, 436/180, 501, 518, 524, 531, 532, 534; 435/6.1, 6.11, 6.19, 7.1, 29, 287.1, 435/287.2, 288.7; 422/527, 528, 82.05
See application file for complete search history.

(56) References Cited

U.S. PATENT DOCUMENTS 5,039,614 A   8/1991  Dekmezian et al.
5,831,723 A   11/1998 Kubota et al.
(Continued)

FOREIGN PATENT DOCUMENTS

AU    3851389 A     1/1990
AU    2003270759 A1  3/2005
(Continued)

OTHER PUBLICATIONS

Wong et al. Analytical Chemistry, vol. 83, Feb. 2, 2011, pp. 1871-1873.*
(Continued)

*Primary Examiner* — Maureen Wallenhorst
(74) *Attorney, Agent, or Firm* — Amin, Turocy & Watson, LLP

(57) ABSTRACT

A device and a method for detecting an analyte in a liquid sample. In an aspect, a mixing portion is configured to receive and mix a first liquid solution of unknown composition with a second liquid solution that includes a suspended particle resulting in a mixed liquid solution, wherein a surface of the suspended particle is functionalized to target an analyte. Furthermore, in an aspect, a surface of a solid substrate is configured to receive and evaporate a drop of the mixed liquid solution, wherein evaporation of the drop in connection with a capillary flow of the mixed liquid solution disperses the suspended particle in a ring pattern. The presence or absence of an analyte in the first liquid solution can be determined by visual inspection of the ring pattern.

35 Claims, 13 Drawing Sheets

(51) Int. Cl.
  *G01N 33/68* (2006.01)
  *G01N 19/08* (2006.01)
  *G01N 21/88* (2006.01)
  *G01N 15/06* (2006.01)
  *G01N 21/84* (2006.01)
  *G01N 1/38* (2006.01)
  *G01N 1/40* (2006.01)
  *G01N 15/00* (2006.01)

(52) U.S. Cl.
  CPC  *G01N1/38* (2013.01); *G01N 19/08* (2013.01); *G01N 21/8483* (2013.01); *G01N 33/68* (2013.01); *G01N 2001/4027* (2013.01); *G01N 2015/0053* (2013.01); *G01N 2015/0065* (2013.01); *G01N 2015/0681* (2013.01)

(56) References Cited

U.S. PATENT DOCUMENTS

| | | | |
|---|---|---|---|
| 7,037,729 | B2 | 5/2006 | Nie et al. |
| 7,648,845 | B2 | 1/2010 | Nie et al. |
| 2005/0032244 | A1 | 2/2005 | Nie et al. |
| 2007/0092978 | A1 | 4/2007 | Mink et al. |
| 2009/0169861 | A1 | 7/2009 | Nie et al. |
| 2012/0276523 | A1 | 11/2012 | Haselton et al. |

FOREIGN PATENT DOCUMENTS

| | | |
|---|---|---|
| CA | 1319539 C | 6/1993 |
| CA | 2534402 A1 | 2/2005 |
| CA | 2626468 A1 | 4/2007 |
| CA | 2534402 C | 6/2013 |
| CN | 1163402 A | 10/1997 |
| CN | 1469111 A | 1/2004 |
| CN | 1161599 C | 8/2004 |
| DE | 69703408 D1 | 12/2000 |
| DE | 69703408 T2 | 3/2001 |
| EP | 0801295 A1 | 10/1997 |
| EP | 0801295 B1 | 11/2000 |
| EP | 1664772 A1 | 6/2006 |
| EP | 1664772 A4 | 1/2007 |
| EP | 1938102 A2 | 7/2008 |
| EP | 1938102 A4 | 6/2009 |
| JP | H09273988 A | 10/1997 |
| JP | 3640461 B2 | 4/2005 |
| JP | 2007521460 A | 8/2007 |
| JP | 2009517632 A | 4/2009 |
| JP | 4491417 B2 | 6/2010 |
| TW | 479137 B | 3/2002 |
| WO | 8912828 A1 | 12/1989 |
| WO | 2005017525 A1 | 2/2005 |
| WO | 2007047924 A2 | 4/2007 |
| WO | 2007047924 A4 | 1/2009 |

OTHER PUBLICATIONS

Li et al. Sensors and Actuators B: Chemical, vol. 206, Sep. 16, 2014, pp. 56-64.*
Haselton, et. al. "Biomarker-Mediated Disruption of Coffee-Ring Formation as a Low Resource Diagnostic Indicator". Langmuir, 2012, 28 (4), pp. 2187-2193.
International Search Report for PCT Application No. PCT/CN2014/084326, dated Feb. 3, 2015, 5 pages.
Written Opinion for PCT Application No. PCT/CN2014/084326, dated Feb. 3, 2015, 4 pages.

* cited by examiner

DETECTION OF ANALYTE USING COFFEE-RING EFFECT

TECHNICAL FIELD

This disclosure generally relates to detecting the presence or absence of an analyte within a liquid solution.

BACKGROUND

Traditionally, the detection of an analyte such as a biomarker requires the use of special equipment. For instance, an analyte can be detected in a sample by capturing a fluorescence signal via a fluorescence device (e.g., UV spectrophotometer) or by administering a colorimetric assay to capture a color via spectrometer, or by detecting an electrochemical current via a current meter. These analyte detection devices and methods along with others use sophisticated detection equipment, skilled technicians to operate the equipment, and access to significant capital amounts to purchase the materials and equipment.

In several locations around the world, there are infectious diseases that cause hundreds of thousands of fatalities each year. For instance, in 2010, malaria affected 216 million people and caused 655,000 deaths. In many cases, the effects of diseases, such as malaria, could be lessened through early diagnosis and detection. Unfortunately, many of the regions where a greater number of the world population suffers from these diseases are impoverished and cannot afford expensive analyte detection equipment. Furthermore, such populations often lack technicians and other personnel with sufficient training to administer and interpret the results of such diagnostic tests. Another problem exists where many of these impoverished communities resort to implementing inaccurate and burdensome detection tests. For example, some detection techniques comprise manual counting of parasites in a patient's blood to diagnose a disease; such detection methods are often inaccurate and time-consuming.

The above-described background relating to medical services and diagnoses is merely intended to provide a contextual overview of some present conditions, and is not intended to be exhaustive. Other context regarding the state of the art may become further apparent upon review of the following detailed description.

SUMMARY

The following presents a simplified summary of various aspects of the disclosed subject matter in order to provide a basic understanding of some aspects described herein. This summary is not an extensive overview of the disclosed subject matter. It is intended to neither identify key or critical elements of the disclosed subject matter nor delineate the scope of such aspects. Its sole purpose is to present some concepts of the disclosed subject matter in a simplified form as a prelude to the more detailed description that is presented later.

In accordance with one or more embodiments and corresponding disclosure, various non-limiting aspects are described in connection with the development of a device to detect the presence or absence of an analyte by inspecting pattern formations remaining upon the evaporation of a liquid solution comprising one or more suspended particle.

In an embodiment, a device is described. In an aspect, the device comprises a mixing portion configured to receive and mix a first liquid solution of unknown composition with a second liquid solution comprising a suspended particle resulting in a mixed liquid solution, wherein a surface of the suspended particle is functionalized to target an analyte. In another aspect, the device employs a surface of a solid substrate configured to receive and evaporate a drop of the mixed liquid solution, wherein evaporation of the drop in connection with a capillary flow of the mixed liquid solution disperses the suspended particle in a ring pattern based on at least one property of the suspended particle defined in relation to a presence of the analyte or an absence of the analyte in the first liquid solution. Furthermore, in an aspect the device employs a processing device configured to inspect image data, received from an imaging element and representing the ring pattern information, and detect the presence of the analyte or the absence of the analyte in the first liquid solution based on at least one property of the ring pattern information.

In another embodiment, a method is described. The method comprises mixing a first liquid solution of unknown composition with a second liquid solution comprising a suspended particle resulting in a mixed liquid solution whereby a surface of the suspended particle is functionalized to target an analyte. In another aspect, the method comprises dispensing a drop of the mixed liquid solution on a surface of a solid substrate. Furthermore, the method comprises evaporating the drop, wherein the evaporating in connection with a capillary flow of the mixed liquid solution disperses the suspended particle in a ring pattern based on at least one property of the suspended particle defined in relation to a presence of the analyte or an absence of the analyte in the first liquid solution. In another aspect, the method comprises the act of detecting the presence of the analyte or the absence of the analyte in the first liquid solution based on an image inspection of the ring pattern and information about the at least one property.

The following description and annexed drawings set forth in detail certain illustrative aspects of the disclosed subject matter. These aspects are indicative, however, of but a few of the various ways in which the principles of the disclosed subject matter may be employed, and the disclosed subject matter is intended to include all such aspects and their equivalents. Other advantages and distinctive features of the disclosed subject matter will become apparent from the following detailed description of the disclosed subject matter when considered in conjunction with the drawings.

BRIEF DESCRIPTION OF THE DRAWINGS

Numerous aspects and embodiments are set forth in the following detailed description, taken in conjunction with the accompanying drawings, in which like reference characters refer to like parts throughout, and in which.

DETAILED DESCRIPTION

Figure 1:
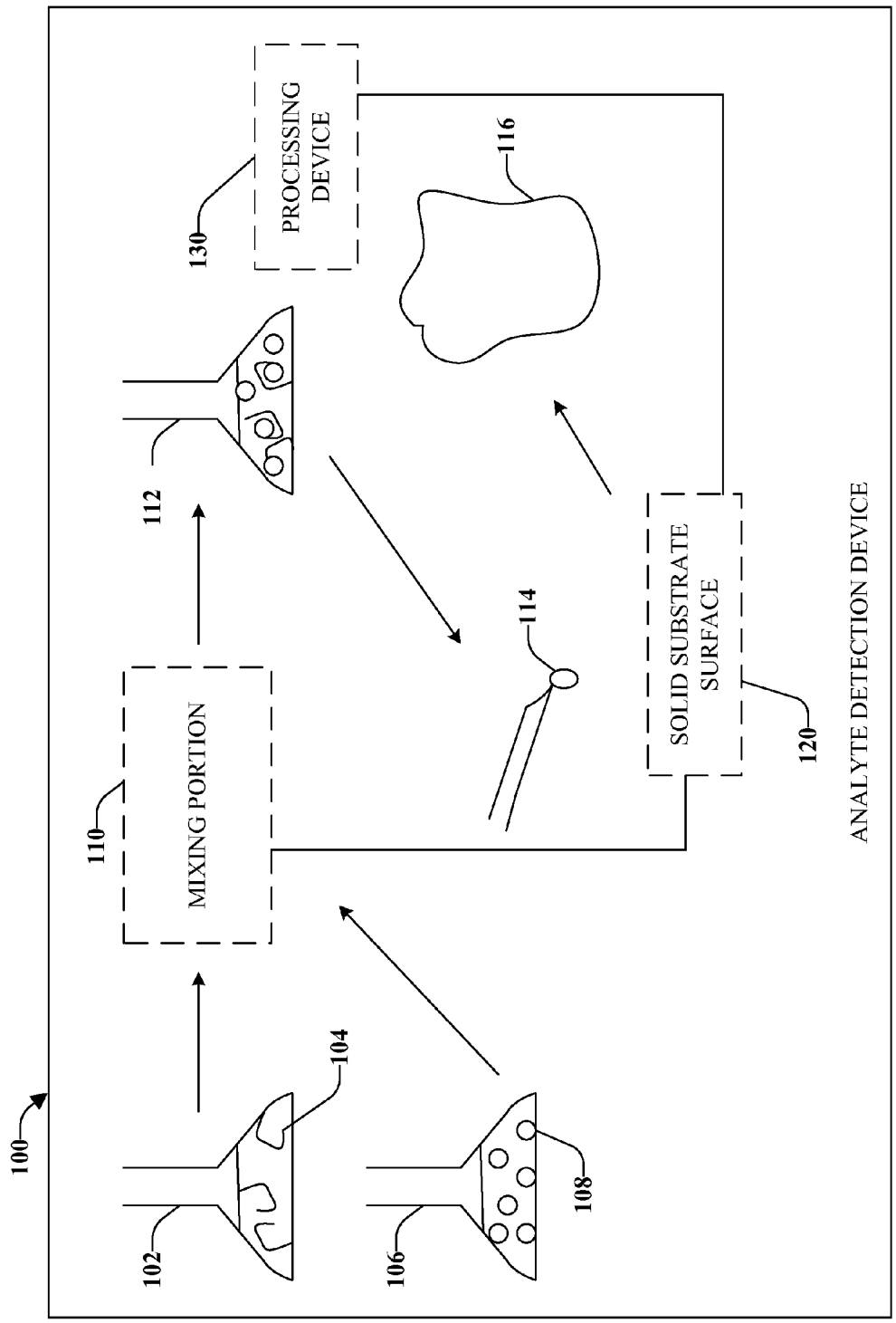
FIG. 1 is an example non-limiting block diagram of a device for detecting the presence or absence of an analyte in a liquid solution by analyzing ring pattern information.

Various aspects or features of this disclosure are described with reference to the drawings, wherein like reference numerals are used to refer to like elements throughout. In this specification, numerous specific details are set forth in order to provide a thorough understanding of this disclosure. It should be understood, however, that the certain aspects of disclosure may be practiced without these specific details, or with other methods, components, molecules, etc. In other instances, well-known structures and devices are shown in block diagram form to facilitate description and illustration of the various embodiments.

As alluded to in the background, low-cost, point-of-care, diagnostic devices and methods are desired that are accessible to parts of the population that lack resources to access effective detection devices. Furthermore, diagnostic devices that are easy to administer and interpret are desired so that even a layperson can diagnose the presence of a disease state by using such device. Additionally, a detection device that can perform many other diagnostic tasks such as detection of environmental toxins (e.g., water toxins, food toxins, etc.) in addition to detection of diseases could greatly benefit these populations by providing the maximum diagnostic utility.

In accordance with one or more embodiments described in this disclosure, a device and method for detecting one or more analyte are described. A mixed liquid solution is evaporated to reveal a pattern formed by remaining suspended particles. The particular pattern formed indicates the presence or absence of an analyte. The ease of use and economical implementation of the analyte detection device and method offers a significant benefit to administrators and users of diagnostic tests in various regions of the world. For instance, a significant number of the world population are impoverished or lack disposable income to purchase sophisticated analyte detection tests, which require special equipment and access to developed medical facilities. In many third world countries, wherein a large segment of the population is impoverished or lives below the poverty line, the people suffer from poor healthcare and are often stricken with disease and illness.

Many of these people are unaware of their illness or lack access to screening mechanisms that would notify them of their condition. The number of individuals suffering from such diseases could be dramatically decreased if they had access to easy to use detection devices. For instance, many people could learn without complex training, how to visually observe a pattern produced by an evaporated liquid to detect the presence of malaria simply by visual inspection of the pattern in comparison to another pattern. Such a simple to use device could enhance the health prospects of the population and provide access to diagnostic services that were previously unavailable to much of the worlds population.

Referring now to the drawings, with reference initially to FIG. 1, illustrated is an example non-limiting schematic block diagram of a device 100. The device 100 comprises a mixing portion 110, a surface of a solid substrate 120, and a processing device 130. In an aspect, the mixing portion 110 is configured to receive and mix a first liquid solution 102 of unknown composition with a second liquid solution 106 comprising a suspended particle 108 resulting in a mixed liquid solution 112, wherein a surface of the suspended particle 108 is functionalized to target an analyte 104. In another aspect, the surface of a solid substrate 120 is configured to receive and evaporate a drop 114 of the mixed liquid solution 112, wherein evaporation of the drop 114 in connection with a capillary flow of the mixed liquid solution 112 disperses the suspended particle 108 in a ring pattern based on at least one property of the suspended particle 108 defined in relation to a presence of the analyte 104 or an absence of the analyte 104 in the first liquid solution 104.

In another aspect, a processing device 130 is configured to inspect image data, received from an imaging element and representing the ring pattern information 116, and detect the presence of the analyte 104 or the absence of the analyte 104 in the first liquid solution 102 based on at least one property of the ring pattern information 116. Ring pattern information 116 can refer to the meaning conveyed by the formation of particles left behind following evaporation of a liquid solution, sometimes referred to as the coffee ring effect. The coffee ring effect refers to a phenomenon whereby one or more suspended particle 108 present in a drop of a liquid solution can form a pattern on a surface (e.g. a table, counter top, etc.) after evaporation. Capillary flow describes the characteristic flow of an evaporating drop 114 of liquid wherein the liquid evaporating at drop 114 edges are replenished by liquid from the interior of drop 114. The resulting outward flow can carry and disperse material within the liquid, such as suspended particle 108, to the edge of drop 114. For example, in an instance the evaporation of a liquid solution comprising suspended particle 108 that are spherical in shape can present a pattern of concentrated spherical particles in the pattern of a ring. The ring pattern information 116 can convey information about a liquid or a sample, such as the presence or absence of an analyte 104. In an instance, an analyte 104 is a substance or chemical constituent that is the subject of analysis. An analyte 104 can be present or absent from a liquid substance such as a biological fluid (e.g., blood, serum, saliva, urine, etc.). For instance, an analyte 104 can be *Plasmodium falciparum* histidine rich protein (also referred to as pf HRPII) wherein detection of the presence of *Plasmodium falciparum* histidine rich protein in a biological sample can indicate the presence of malaria in the donor of the biological sample. Thus detection of the presence of an analyte 104 in a biological sample can provide significant diagnostic information to a user.

The presence of analyte 104 can be determined by inspection of a particular pattern formed by one or more suspended particle 108 upon evaporation of a drop of a liquid. A medical professional, technician or person with minimal training can diagnose the presence of malaria in a person whom provides a biological sample for analysis simply by observing the remaining pattern from the one or more suspended particle 108. It is apparent, for instance, that device 100 can facilitate patient access to early diagnosis of malaria, which is curable if treated early.

In an aspect, device 100 comprises a mixing portion 110 which is configured to receive and mix a first liquid solution 104 of unknown composition with a second liquid solution 106 comprising a suspended particle 108 resulting in a mixed liquid solution 112. In an aspect, the mixing portion 110 can be a receptacle such as a container, flask, chamber, bowl, cylinder, or other such tool capable of storing a liquid. The mixing portion 110 can mix received liquids. In an aspect, the mixing can occur automatically (e.g., via a mechanical motor operated mixing spoon or other such mechanism) or manually (e.g., stirring, mixing or swirling the contents of mixing portion 110). In an aspect, the mixing portion 110 is configured to mix a first liquid solution 102 of unknown composition and a second liquid solution 106 comprising a suspended particle 108. A first liquid solution 102 can be any liquid of unknown composition. For instance, the first liquid solution 102 can be a biological sample wherein the device 100 can detect the presence or absence of an antigen that indicates a disease profile associated with the presence or absence of the antigen. In another aspect, the first liquid solution 102 can be a sample of environmental water wherein the device 100 can detect the presence or absence of an antigen that indicates the presence or absence of a pollutant or toxin in the water sample.

In another aspect the first liquid sample 102 can be a liquefied sample of a food item, wherein the device 100 can detect the presence or absence of an antigen that indicates a safety or health profile for the sample food item. The first liquid sample 102 can be any of a variety of liquid samples (e.g., water, blood, urine, etc.) of unknown contents sought for testing. The suspended particle 108 present in the second liquid solution 106 can be customized to target a defined analyte 104 suspected to be present in the first liquid sample 102. The suspended particle 108 can be customized to target and bind to analyte 104 based on the chemical properties of the analyte 104 to be detected. The binding can occur via covalent chemical bonds, physical forces (e.g., Van der Waals forces), ionic bonds, and other such linking mechanisms. For instance, the second liquid solution 106 can comprise a suspended particle 108 conjugated to an antigen complimentary to an analyte 104 targeted for detection. As such, suspended particle 108 can be functionalized to comprise a functional group tailored to the surface of the suspended particle 108 wherein the functional group can itself target, attract, or bind to a target analyte 104. In another aspect, a functional group can be a ligand molecule, specific grouping of compounds, or other such chemical element located at the surface of the suspended particle 108 whereby the functional group is capable of binding to an analyte targeting agent that thereby targets analyte 104.

In an aspect, the functional group is capable of binding to an analyte targeting agent such as an mRNA, oligonucleotide, protein, or other such biomarker. Furthermore, such targeted analyte 104 can also be an mRNA, oligonucleotide, protein, or other such biomarker. The binding of a functional group or analyte-targeting agent to such biomarkers can facilitate disease diagnosis for many types of diseases, such as infectious diseases or cancers. For instance, many oral cancer patients are known to present elevated levels of seven signature mRNA in saliva samples. By functionalizing the surface of one or more suspended particle 108 to bind to the seven particular mRNA, the detection of oral cancer in patients can be performed at a point-of-care diagnostic setting (e.g., by detecting one or more of the seven signature mRNA in a patient sample). Furthermore, suspended particle 108 can be comprised of particles of varying sizes and shapes whereby each particle of a particular size or shape can be functionalized to target a different analyte 104. Thus, the detection of multiple analyte 104 can be accomplished by device 100. For example, seven respective suspended particle 108 can be uniquely tailored (e.g., with respective functionalized surfaces or mRNA targeting agents) to target seven unique mRNA respectively.

In an aspect, suspended particle 108 can be a microsphere which are spherical particles comprising diameters ranging from 1 to 1000 micrometers. Microspheres can be comprised of a number of natural or synthetic materials (e.g., glass, ceramic, metal, polyethylene, semiconductor materials, etc.). In an aspect, suspended particle 108 can be an ellipsoid in shape and of micrometer dimensions. An ellipsoid has a length greater than the principal axis and a diameter greater than the minor axis. Furthermore, suspended particle 108 can take the shape of various non-spherical or non-ellipsoid heterostructures. The shape properties of suspended particle 108 can influence the expected pattern formation in the presence or absence of analyte 104. In an aspect, the suspended particle 108 can be comprised of spherical particles or non-spherical particles. In an aspect, device 100 can be versatile in detecting various diseases using different shaped suspended particle 108.

In an aspect, device 100 can employ suspended particle 108 and its targeting capabilities to detect environmental toxins. In an aspect, the surface of suspended particle 108 can be functionalized to bind to metal ions or Botulinum toxin whereby the functional group can be an aptamer. In such instance, device 100 can serve as a platform for environmental screening tasks such as identifying toxins in drinking water or identifying various chemical compositions of rainwater. Device 100 can be versatile in its detection applications, which provides additional benefit to the end users.

In an aspect, device 100 employs a surface of a solid substrate 120 which is configured to receive and evaporate a drop 114 of the mixed liquid solution 112, wherein evaporation of the drop 114 in connection with a capillary flow of the mixed liquid solution disperses the suspended particle 108 in a ring pattern based on at least one property of the suspended particle 108. For instance, suspended particle 108 in the presence of an analyte 104 can bind to the analyte 104 and alter the shape of the suspended particle 108. As an example, wherein suspended particle 108 is a microsphere particle, the binding of the microsphere particle to an analyte creates a new shape of the microsphere as a result of the linkage with analyte 104. Furthermore, in an aspect, the microsphere linked to an analyte may resist capillary flow of the evaporating liquid in a different manner than the microsphere absent binding to an analyte 104 thereby dispersing the suspended particle 108 at a different region of the evaporated drop than in the absence of analyte 104. The pattern of dispersion of the suspended particle 108 can be observed following the evaporation of drop 114 on the solid substrate 120.

In an aspect, solid substrate 120 can be a variety of solid-state materials such as a metal surface, glass surface, or other solid substances. The solid substrate 120 is capable of receiving a drop 114 of the mixed liquid solution 112. A liquid dispenser such as a dropper, glass tube, or other applicator capable of dispensing a liquid drop can be used to drip a drop 114 of the mixed liquid solution 112 on the surface of the solid substrate 120. Furthermore, the drop 114 can be left to evaporate over time until only a formation of dispersed suspended particle 108 remain in the form of a particular pattern. The particular pattern formed conveys ring pattern information 116. The ring pattern information 116 will indicate the presence or absence of analyte 104.

In an aspect, the shape of suspended particle 108 effects the movement of a respective suspended particle 108 in connection with capillary flow of evaporating drop 114. For instance, a spherical microparticle can flow to the edge of the drop 114 where the surface of the solid substrate 120 meets the drop 114. Conversely, non-spherical ellipsoid or particle aggregate creates higher resistance to the capillary flow. This in turn can cause the one or more suspended particle 108 to deposit, upon evaporation of drop 114, at a location other than the edge of the drop 114 thus distorting or terminating the appearance of a ring pattern.

In another aspect, the dispersion of suspended particle 108 can face varying degrees of resistance to the capillary flow depending on the size, shape, or inter-particle forces of one or more suspended particle 108. In an aspect, one or more suspended particle 108 can aggregate together or segregate apart at varying degrees depending on the size or shape of the suspended particle 108. In an aspect, the aggregation or segregation of one or more suspended particle 108 can create greater or lesser levels of resistance to capillary flow thereby affecting the distribution and movement of the one or more suspended particle 108 upon drop 114 evaporation. The dispersion can be based on various properties of the particles such as structure or shape of aggregate suspended particles 108.

Furthermore, in an aspect, the resistance of the suspended particle 108 to capillary flow can be altered based on the variations of suspended particle 108 within mixed liquid solution 112. For instance, wherein mixed liquid solution 112 comprises spherical shaped suspended particle 108 and ellipsoid shaped suspended particle 108, the resistance to the capillary flow of the suspended particle can be different as compared to the resistance to the capillary flow of a mixed liquid solution 112 that comprises one or more suspended particle 108 solely spherical in shape. The resistance can be based on a number of factors such as the shape of suspended particle 108, surface drag of suspended particle 108 (alone or in aggregate) to the liquid environment of drop 114, the density of the liquid portion of mixed liquid solution 112, the bulk flow of one or more aggregated suspended particle 108, the surface property of suspended particle 108, the surface tension of drop 114, or the dimensions (e.g., height) of drop 114.

Furthermore, in an aspect, the binding of suspended particle 108 to analyte 104 can cause multiple suspended particle 108 to aggregate or segregate and create greater or lesser levels of resistance to capillary flow and therefore enhance or suppress movement to reaching the point of contact between the solid substrate 120 surface and the edge of drop 114. In an aspect, wherein suspended particles 108 are spherical in shape, suspended particle 108 can flow to the edge of the drop 114 where the surface of the solid substrate 120 meets the drop 114. The lower resistance to capillary flow enables the spherical particles to accumulate at the point of contact between the solid substrate 120 surface and the drop 114 edges thereby creating a ring pattern as per the coffee ring effect. In another aspect, binding of suspended particle 108 to analyte 104 may cause the particle aggregation. The non-spherical shaped particle aggregates create greater resistance to capillary flow thereby distorting the appearance of a ringed dispersion pattern upon evaporation of drop 114.

In an aspect, device 100 can differentiate between different patterns formed by the suspended particle 108 following evaporation of drop 114 based on factors such as; type of suspended particle 108 incorporated into mixed liquid solution 112, the customized functionalization of the suspended particle 108 surface, or the analyte 104 to be detected. In an aspect, such variables can contribute to the formation of particular patterns (e.g., a ring pattern, an augmented ring pattern, no ring pattern, a disperse pattern of suspended particle 108, etc.) that indicate the presence or absence of an analyte 104 in first liquid solution 102 upon evaporation of drop 114.

In another aspect, device 100 employs a processing device 130 that can be configured to inspect image data, received from an imaging element and representing the ring pattern information 116, and detect the presence of analyte 104 or the absence of analyte 104 in first liquid solution 102 based on at least one property of ring pattern information 116. In another aspect, processing device 130 can be an instrument that creates an image of ring pattern information 116 via an imaging element (e.g., camera lens) wherein the image can be inspected to determine the presence or absence of analyte 104 in first liquid solution 102. The image can comprise pixels represented in a digital format. In an aspect, the image data can be used to analyze the ring pattern information 116 in significant specificity such as analyte 104 concentration levels, inter-particle structural assessments of suspended particle 104, or compositional makeup of the dispersed matter.

However, as mentioned above, a significant benefit of device 100 is that no equipment is required for detecting the presence or absence of analyte 104. In an aspect, upon visual inspection, without the use of any tool, a person can observe the ring pattern information 116 and determine the presence or absence of an analyte 104 based on visual inspection of ring pattern information 116. For instance, a liquid drop comprising only microspheres can expect to evaporate and present a ring pattern resembling a coffee ring. However, if the microsphere liquid is mixed with a sample possibly containing a suspected analyte and upon evaporation a drop of the mixed liquid the ring pattern is destroyed or distorted, then a person can determine the presence of the analyte upon visual inspection of the ring deformity. Thus, processing device 130 can be individual observation by a person to process the ring pattern information 116 and determine the presence or absence of analyte 104. Given its needlessness for sophisticated interpretation equipment, device 100 can be very beneficial for preliminary screening or detection of a disease in a multitude of disease stricken regions around the world. Also, due to its ease of use, a technician or medical personnel in a rural area or impoverished community can, with little training, use device 100 for early diagnosis of various diseases. Furthermore, in an aspect, a technician with little training can detect toxins in the environment or in food samples thereby enhancing the health prospects of affected communities.

Since inspection of the ring pattern information 116 and detection of the presence or absence of analyte 104 can be performed via visual inspection in bright field or with the naked eye, device 100 can provide an easy to use and cost-effective point of care detection tool to a large population of consumers.

Figure 2A:
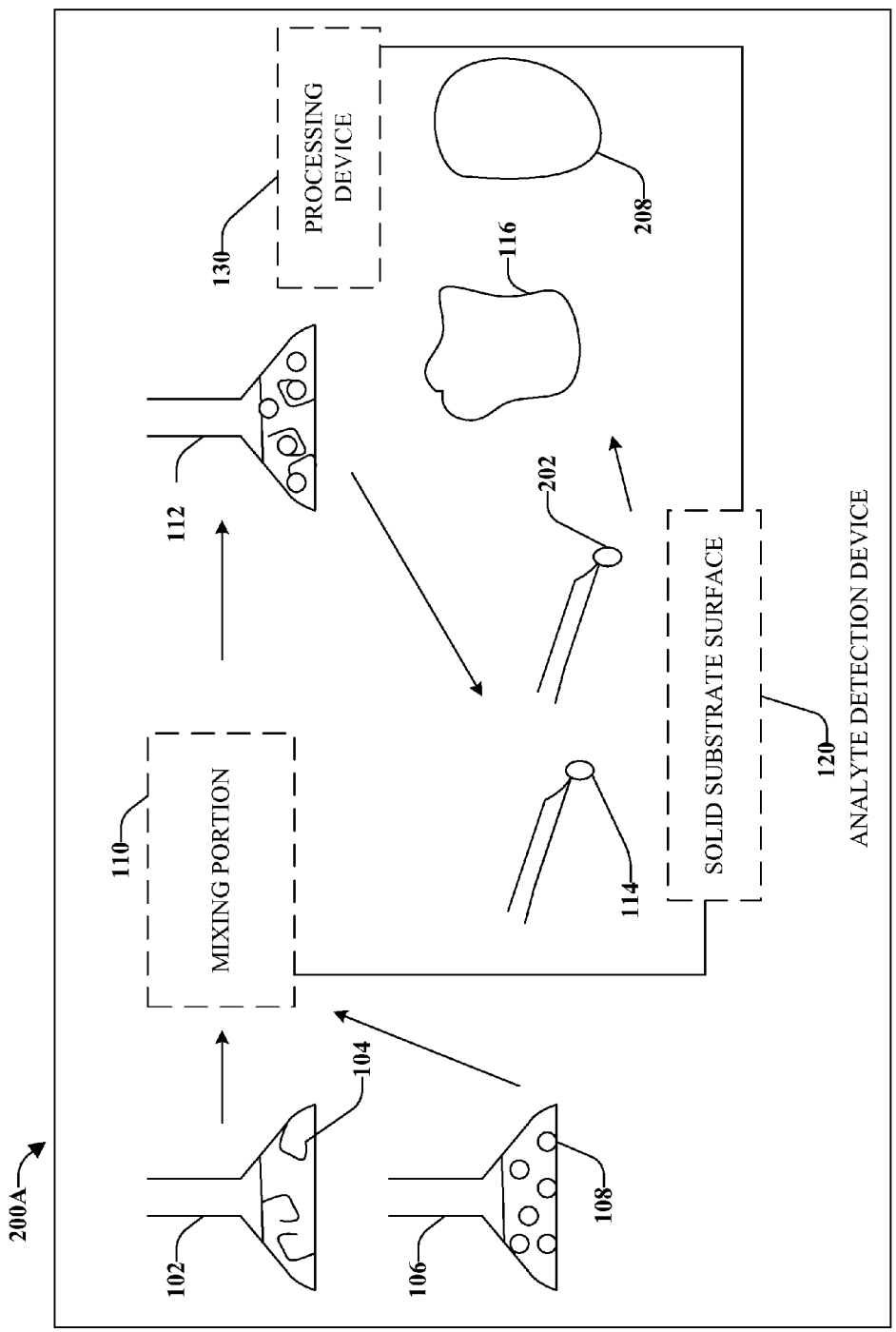
FIG. 2A is an example non-limiting block diagram of a device for detecting the presence or absence of an analyte in a liquid solution by comparing a first ring pattern to a second ring pattern.

Turning now to FIG. 2A, illustrated is an example non-limiting schematic block diagram of device 200A. In an aspect, device 200A comprises a mixing portion 110 configured to receive and mix a first liquid solution 102 and a second liquid solution 106 comprising a suspended particle 108 resulting in a mixed liquid solution 112, wherein a surface of the suspended particle 108 is functionalized to target an analyte 104 within the first liquid solution 102. In another aspect, device 200 is comprised of a surface of a solid substrate 120 configured to receive and allow evaporation of a first drop 114 of the mixed liquid solution 112 onto a surface of a solid substrate 120 and a second drop 202 of the second liquid solution 106. In yet another aspect, device 200A is comprised of a processing device 130 configured to analyze image data, received from an imaging element and representing a first ring pattern information 116 remaining after evaporation of the first drop 214 and a second ring pattern information 208 remaining after evaporation of the second drop 202. In yet another aspect, device 200 can further comprise a processing device 130 configured to detect via a detection element at least one of an enhancement of the second ring pattern information 208 as compared to the first ring pattern information 116 or a diminution of the second ring pattern information 208 as compared to the first ring pattern information 116 based on a change in dispersion of the suspended particle 108 to determine a presence or an absence of analyte 104 based on the image data.

In an aspect, device 200A facilitates the detection of an analyte 104 in first liquid solution 102 via comparative inspection of first ring pattern information 116 as compared to second ring pattern information 208. The comparison of the two ring patterns can reveal differences in the dispersion of the suspended particle 108 and such differences can indicate the presence or absence of analyte 104 in first liquid solution 102. In an aspect, suspended particle 108 can originally be segregated or aggregated relative to other suspended particle 108, prior to mixing (e.g., using mixing portion 110), wherein the segregation or aggregation is based on the properties of the suspended particle 108. For instance, evaporation of drop 114 or drop 202 drives a capillary flow that carries one or more suspended particle 108 toward the respective drop periphery. The pattern formation resulting from the evaporation can depend on the shape of suspended particle 108. For instance, non-spherical ellipsoid particles are observed to have higher resistance to capillary flow and can arrest coffee ring formation (e.g., the non-spherical ellipsoid particles do not move to the farthest periphery of the drop or the non-spherical ellipsoid particles deposit at various non-peripheral locations throughout the drop).

In an aspect, a mixed liquid solution 112 can comprise surface functionalized suspended particle 108 bound to analyte 104. The binding or reaction between the surface functionalized suspended particle 108 and analyte 104 can enhance or reduce inter-particle reactions (e.g., strengthening or weakening inter-particle forces) amongst suspended particle 108 resulting in aggregation or segregation among suspended particle 108 which is demonstrated in the respective pattern formation. In an aspect, liquid solution 102 can be a biological sample such as blood, serum, plasma, saliva, urine, or other such biological material. Furthermore, in an aspect, the analyte sought for detection can be a nucleic acid, protein, chemical compound, metal ion, toxin (e.g., Botulinum toxin), or other such analyte. In an aspect, the inter-particle reactions among the one or more suspended particle 108 can occur via a variety of mechanisms such as DNA/RNA hybridization, protein absorption, immune-affinity, or change of particle surface charge. In an aspect, the changes in particle properties, due to inter-particle reactions for example, prior to mixing liquid solutions and subsequent to mixing liquid solutions can be observed by comparing resultant ring patterns.

In an aspect, device 200A employs mixing portion 110 to receive and mix a liquid solution comprising one or more suspended particle 108 resulting in mixed liquid solution 112.

A first drop 114 of mixed liquid solution 112 is dripped onto and received at the surface of solid substrate 120. Furthermore, the surface of solid substrate 120 receives second drop 202 comprised of a liquid drop of the second liquid solution 106 comprising one or more suspended particle 108. Both drops are evaporated and the evaporation of first drop 114 reveals first ring pattern information 116 whereas evaporation of second drop 202 reveals second ring pattern information 208. In an aspect, visual inspection of first ring pattern information 116 presents a pattern of one or more suspended particle 108 absent a reaction with first liquid solution 102.

The remaining material from the evaporation of second drop 202, which represents a sample of second liquid solution 106 comprising one or more suspended particle 108 conveys information about the one or more suspended particle 108 inter-particle reactions. For instance, second ring pattern 208 illustrates a pattern that resembles a ring-like deposit around the peripheral edges of second drop 202. The coffee ring shaped pattern can indicate that the suspended particle 108 are spherical microspheres which often disperse at the periphery of a drop due to the lower resistance to capillary flow of spherical shaped particles. In an aspect, a suspended particle 108 (e.g., spherical microsphere) that binds to analyte 104 can face greater resistance against capillary flow than a spherical microsphere absent binding to analyte 104. Thus, first ring pattern information 116 is distorted and does not resemble a ring shaped pattern. Thus, the distorted shape of first ring pattern information 116 can indicate the presence of an analyte 104. Via visual inspection, a person such as a technician can observe the comparative difference between first ring pattern information 116 and second ring pattern information 208 to determine the presence or absence of an analyte.

For instance, in the described example, wherein first ring pattern information 116 resembles second ring pattern information 208, a person with little training can determine the absence of an analyte 104 in the second liquid solution 102. However, wherein the first ring pattern information 116 and second ring pattern information 208 demonstrate significant variances, a trained person can determine the presence of the target analyte 104 in the first liquid solution 102 due to changes in the properties of the suspended particle 108 in the presence of analyte 104. A change in particle property (e.g., such as shape or charge) can result in the particle possessing a higher or lower resistance to capillary flow of the evaporating liquid. In an aspect, a suspended particle 108 in the presence of an analyte due to change in shape of the suspended particle 108 bound to analyte 104 or changes in surface charge of suspended particle 108 (e.g., a difference in net charge of the particle due to an increase or decrease in electron or proton count in the presence of analyte 104 or other suspended particle 108) can flow at different speeds or end up in separate locations post-evaporation.

In an aspect, the disclosed analyte detection devices allow for the assembly of one or more suspended particle 108 merely by suspending one or more particles of particular shape and size or of various shapes and size into a liquid. The use of different sized and shaped particles creates an altered resistance to capillary flow after the particles segregate apart or aggregate together. This method does not require the use of external forces such as imposing forces between magnetic and non-magnetic particles or by applying an external magnet to a substrate wherein a drop remains for evaporation. The analyte detection devices do not require the application of fluorescence illumination to observe pattern formations, instead visual observation by the naked eye is sufficient to observe pattern changes and conclude the presence or absence of an analyte in sample.

In another aspect, DNA hybridization can be used to enhance the particle-to-particle interconnection between one or more suspended particle 108. In an aspect, the suspended particle 108 can be bound to an oligonucleotide wherein the oligonucleotide acts as an analyte 104 recognition agent attached to suspended particle 108, wherein the suspended particle 108 can be a microsphere. The oligonucleotide can recognize a target analyte 104, such as a target oligonucleotide of a particular sequence thus enhancing the interconnection between the targeting agent oligonucleotide and the target oligonucleotide via DNA hybridization. The DNA hybridization occurs where the target oligonucleotide is complimentary to the detection oligonucleotide coupled to the microsphere. Upon meeting of the complimentary oligonucleotides, DNA hybridization occurs. As a control, a liquid solution comprising only microspheres and lacking target oligonucleotide formed a natural ring shaped pattern upon evaporation of a drop of the liquid solution. In contrast, the liquid solution comprising only microspheres was mixed with a liquid solution of target oligonucleotide at a concentration of $10^{-5}$ M of target oligonucleotide in the liquid solution. Upon evaporation of the a drop of the mixed solution, the natural ring shaped pattern was eliminated due to the enhanced particle aggregates formed from the binding of the microsphere coupled with analyte targeting oligonucleotide in the presence of the target analyte oligonucleotide.

In an aspect, the type of analyte 104 to be detected can be diverse. The suspended particle 108 can be coupled to a variety of analyte recognition agents in order to target a variety of respective analyte. In instances wherein the change in inter-particle force from the original state of the suspended particle 108 (e.g., an uncoupled suspended particle 108) to the coupled state of the suspended particle 108 (e.g., a suspended particle 108 coupled to an analyte 104) is sufficient to induce aggregation or segregation among one or more suspended particle 108, device 100 and device 200 can be very effective for detection of an analyte. Furthermore, device 100 and device 200 are advantageously portable, energy efficient, and user friendly.

In an embodiment, device 100 and device 200A can provide a portable point-of care device for medical examination. In another aspect, device 100 and device 200 can be an assay kit capable of mixing with an analyte solution, evaporating on a solid substrate surface, and forming a ring pattern following evaporation. For instance, traditionally, detection of malaria required manually counting parasites from patients' blood, which could be inaccurate and time-consuming. Given the disclosed devices, patients' serum samples can be tested for *Plasmodium falciparum* histidine rich protein (pf HRPII), which is present in patients with malaria, via the analyte detection devices, which are more accurate, convenient, economical, and accessible than current detection devices. In another embodiment, the disclosed devices can be a readily accessible platform for detecting environmental toxin, metal ions, or chemicals of various compositions. For instance, the presence of a few grams of Botulinum neurotoxin (BoNT) in an environment proximally located near people can lead to a large number of fatalities. The disclosed devices can monitor and detect an amount of toxin analyte for environmental, food, or water safety applications.

Figure 2B:
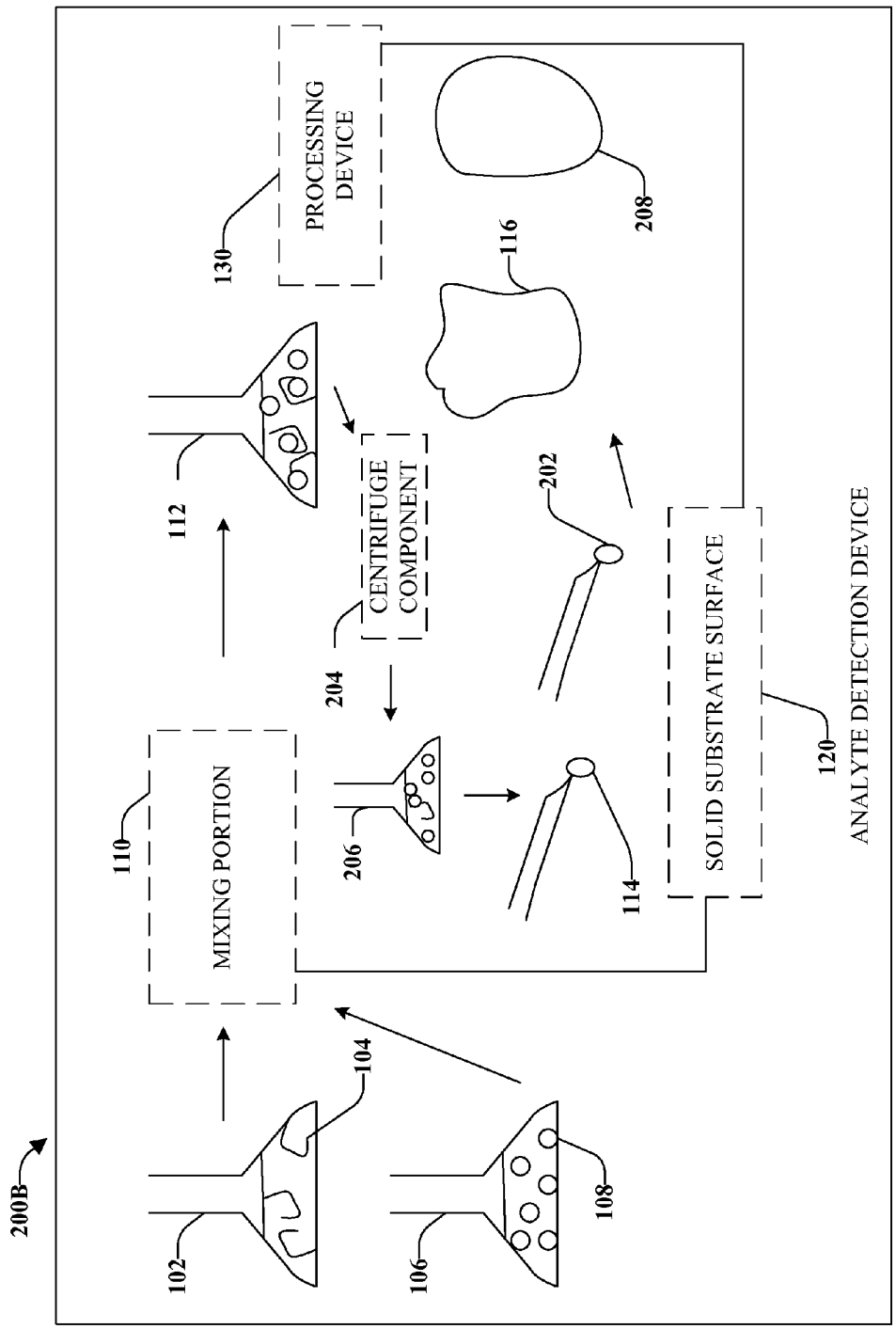
FIG. 2B is an example non-limiting block diagram of a device for detecting the presence or absence of an analyte in a liquid solution by comparing a first ring pattern to a second ring pattern.

Turning now to FIG. 2B, illustrated is an example non-limiting schematic block diagram of device 200B. In an aspect, device 200B comprises a mixing portion 110 configured to receive and mix a first liquid solution 102 and a second liquid solution 106 comprising a suspended particle 108 resulting in a first mixed liquid solution 112, wherein a surface of the suspended particle 108 is functionalized to target an analyte 104 within the first liquid solution 102. In another aspect, a sample of the first mixed liquid solution 112 can be dispensed (e.g., via a dropper, pipette, micropipette, etc.) into a test tube for insertion within a chamber of centrifuge component 204. Further, centrifuge component 204 can spin or rotate the test tube in the centrifuge to concentrate particle 108 at the bottom, and then particle 108 at the bottom can be re-suspended via a dropper, pipette, micropipette, etc, in the same tube. The centrifuge and resuspension can be conducted for one or more cycles resulting in a second mixed liquid solution 206.

In another aspect, device 200B is comprised of a surface of a solid substrate 120 configured to receive and allow evaporation of a first drop 114 of the second mixed liquid solution 206 onto a surface of a solid substrate 120 and a second drop 202 of the second liquid solution 106. In yet another aspect, device 200B is comprised of a processing device 130 configured to analyze image data, received from an imaging element and representing a first ring pattern information 116 remaining after evaporation of the first drop 214 and a second ring pattern information 208 remaining after evaporation of the second drop 202. In yet another aspect, device 200 can further comprise a processing device 130 configured to detect via a detection element at least one of an enhancement of the second ring pattern information 208 as compared to the first ring pattern information 116 or a diminution of the second ring pattern information 208 as compared to the first ring pattern information 116 based on a change in dispersion of the suspended particle 108 to determine a presence or an absence of analyte 104 based on the image data.

Figure 2C:
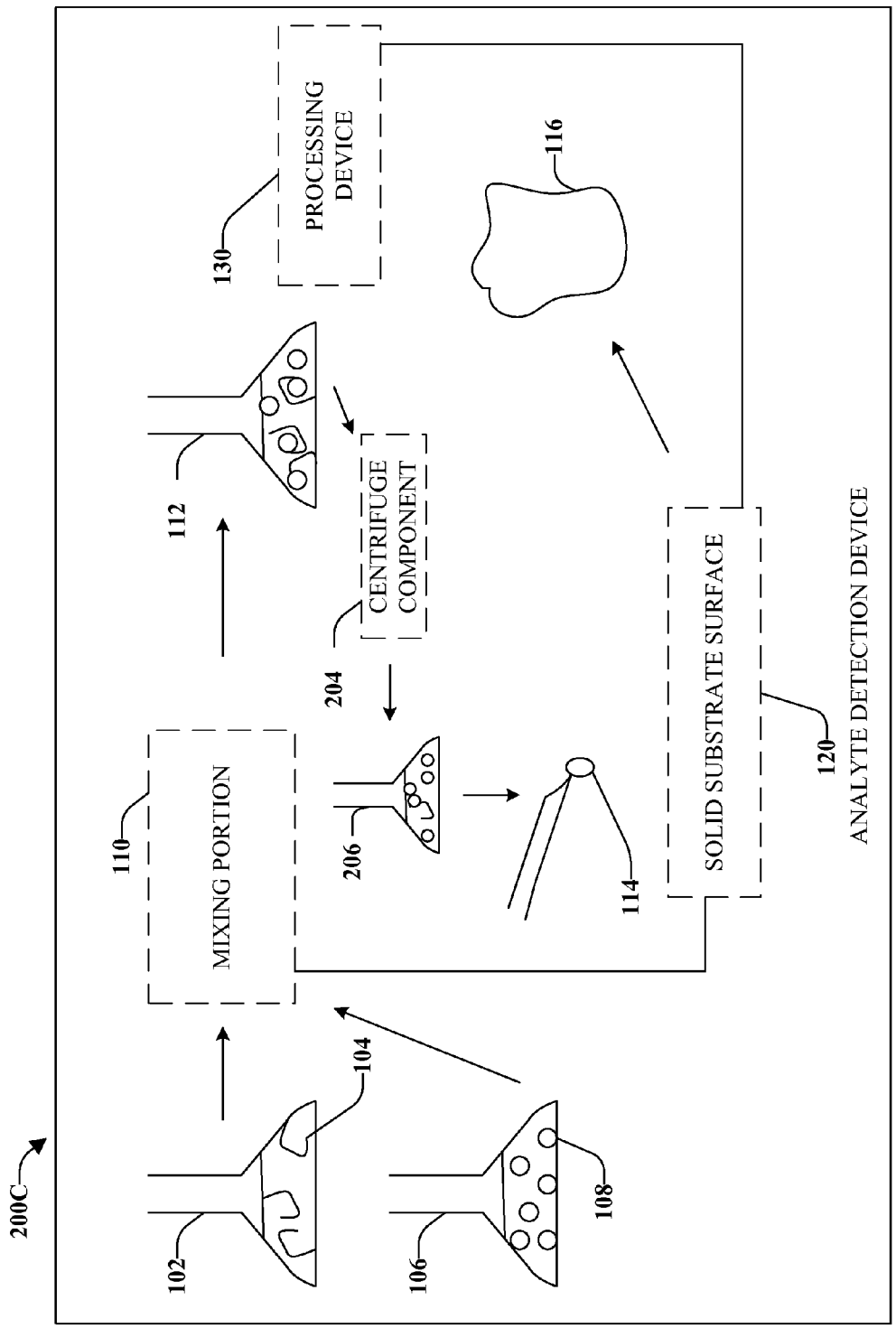
FIG. 2C is an example non-limiting block diagram of a device for detecting the presence or absence of an analyte in a liquid solution by analyzing ring pattern information.

Turning to FIG. 2C, illustrated is an example non-limiting schematic block diagram of device 200C. In an aspect, device 200C comprises a mixing portion 110 configured to receive and mix a first liquid solution 102 and a second liquid solution 106 comprising a suspended particle 108 resulting in a first mixed liquid solution 112, wherein a surface of the suspended particle 108 is functionalized to target an analyte 104 within the first liquid solution 102. In another aspect, a sample of the first mixed liquid solution 112 can be dispensed (e.g., via a dropper, pipette, micropipette, etc.) into a test tube for insertion within a chamber of centrifuge component 204. Further, centrifuge component 204 can spin or rotate the test tube in the centrifuge to concentrate particle 108 at the bottom, and then particle 108 at the bottom can be re-suspended via a dropper, pipette, micropipette, etc, in the same tube. The centrifuge and resuspension can be conducted for one or more cycles resulting in a second mixed liquid solution 206.

In another aspect, device 200B is comprised of a surface of a solid substrate 120 configured to receive and allow evaporation of a first drop 114 of the second mixed liquid solution 206 onto a surface of a solid substrate 120. In yet another aspect, device 200C is comprised of a processing device 130 configured to analyze image data, received from an imaging element and representing a first ring pattern information 116 remaining after evaporation of the first drop 114. In yet another aspect, device 200C can further comprise a processing device 130 configured is configured to inspect image data, received from an imaging element and representing the ring pattern information 116, and detect the presence of the analyte 104 or the absence of the analyte 104 in the first liquid solution 102 based on at least one property of the ring pattern information 116.

Figure 3:
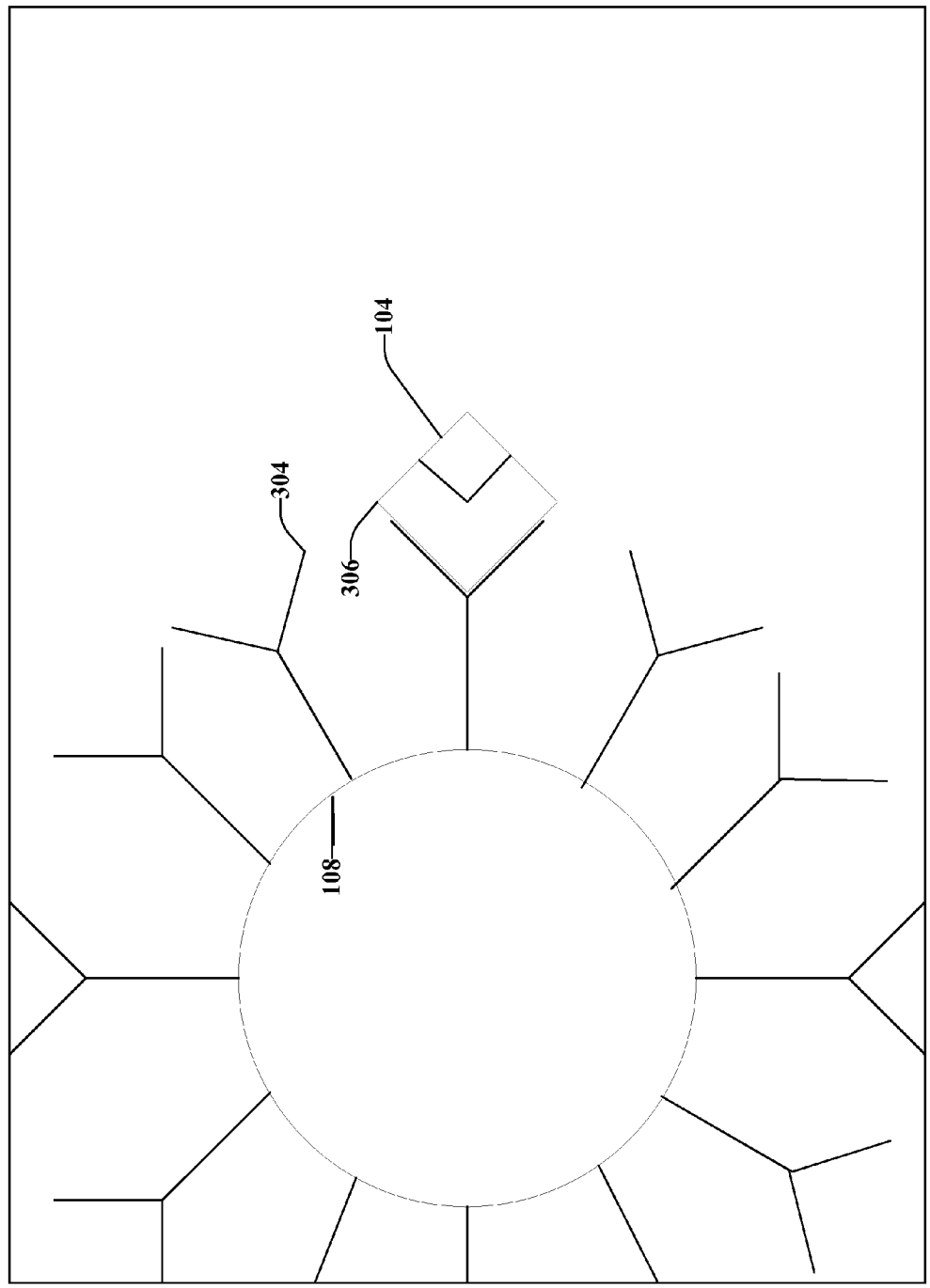
FIG. 3 is an example non-limiting illustration of a suspended particle coupled to an analyte.

Referring now to FIG. 3, illustrated is an example non-limiting suspended molecule 108. In an aspect, suspended molecule 108 is surface functionalized with a chemical functional group 304 such as an alcohol, carboxylate, amine, hydroxyl, nitrate, phosphate, or sulfonate. In an aspect, more than one functional group can be present on the surface of suspended molecule 108 wherein each functional group can couple to an analyte-targeting agent 306. In an aspect the analyte targeting agent 306 can be an antibody, antigen, protein, protein receptor, drug receptor, drug, peptide receptor, peptide, protein receptor, protein, oligonucleotide, DNA, RNA, enzyme, nucleic acid, polymer, lipid or other non-limiting analyte-targeting agent 306. In an aspect, an analyte-targeting agent 306 can target an analyte 104 by bonding (e.g., ionic bond, covalent bond, Van der Waals forces, etc.) to the analyte 104.

The complimentary nature of analyte-targeting agent 306 and analyte 104 not only facilitates the linking between suspended particle 108 and analyte 104 but also changes the shape of suspended particle 108 and thus the properties of the particle as well. Thus the resistance to capillary flow of a suspended particle 108 coupled to an analyte 104 can differ from the resistance to capillary flow of an unbound suspended particle 108. Such differences can cause differences in ring pattern formations and thereby indicate the presence or absence of an analyte in a sample liquid based on such ring patterns.

Figure 4:
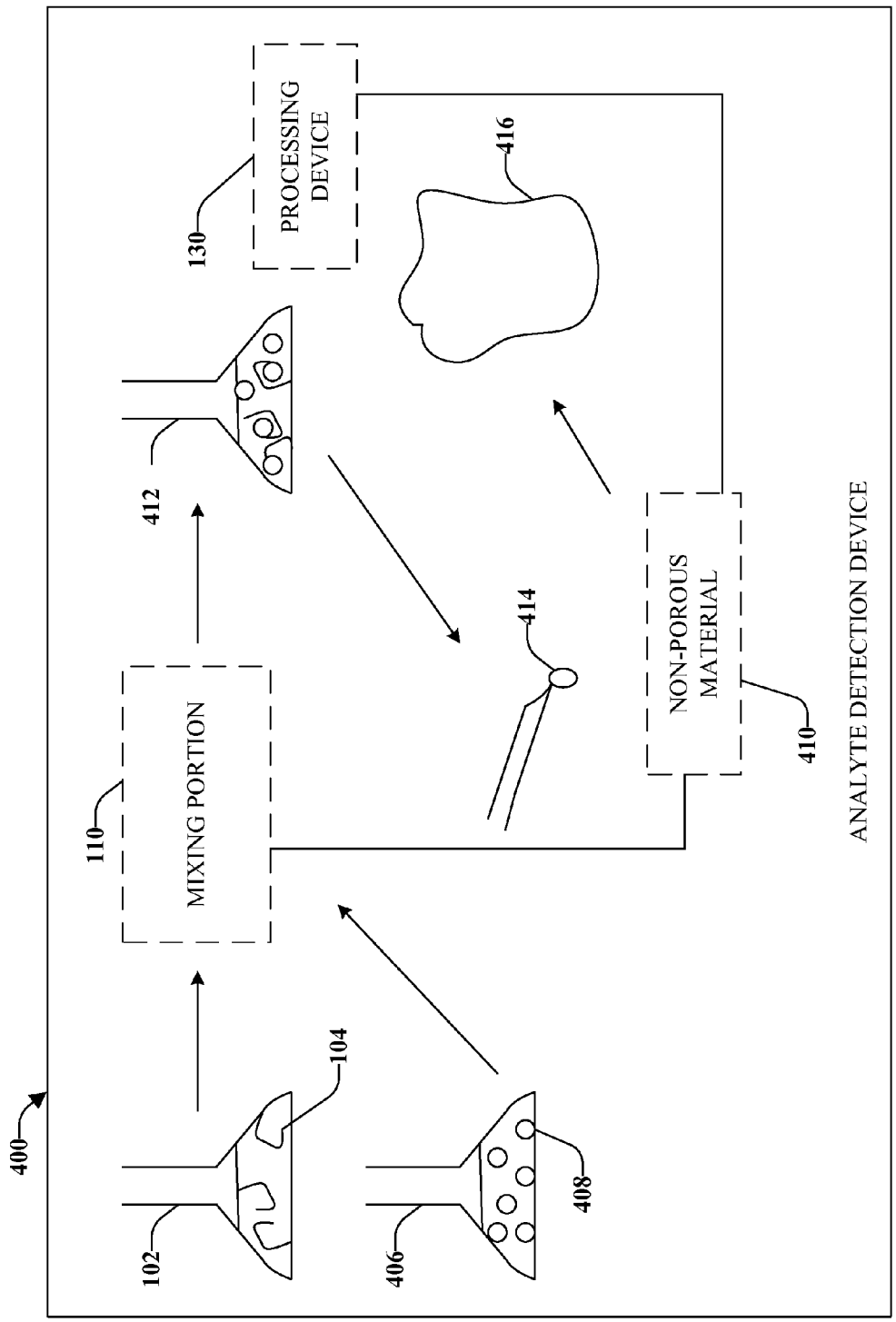
FIG. 4 is an example non-limiting block diagram of a device for detecting the presence or absence of an analyte in a liquid solution by analyzing ring pattern information.
Figure 5A:
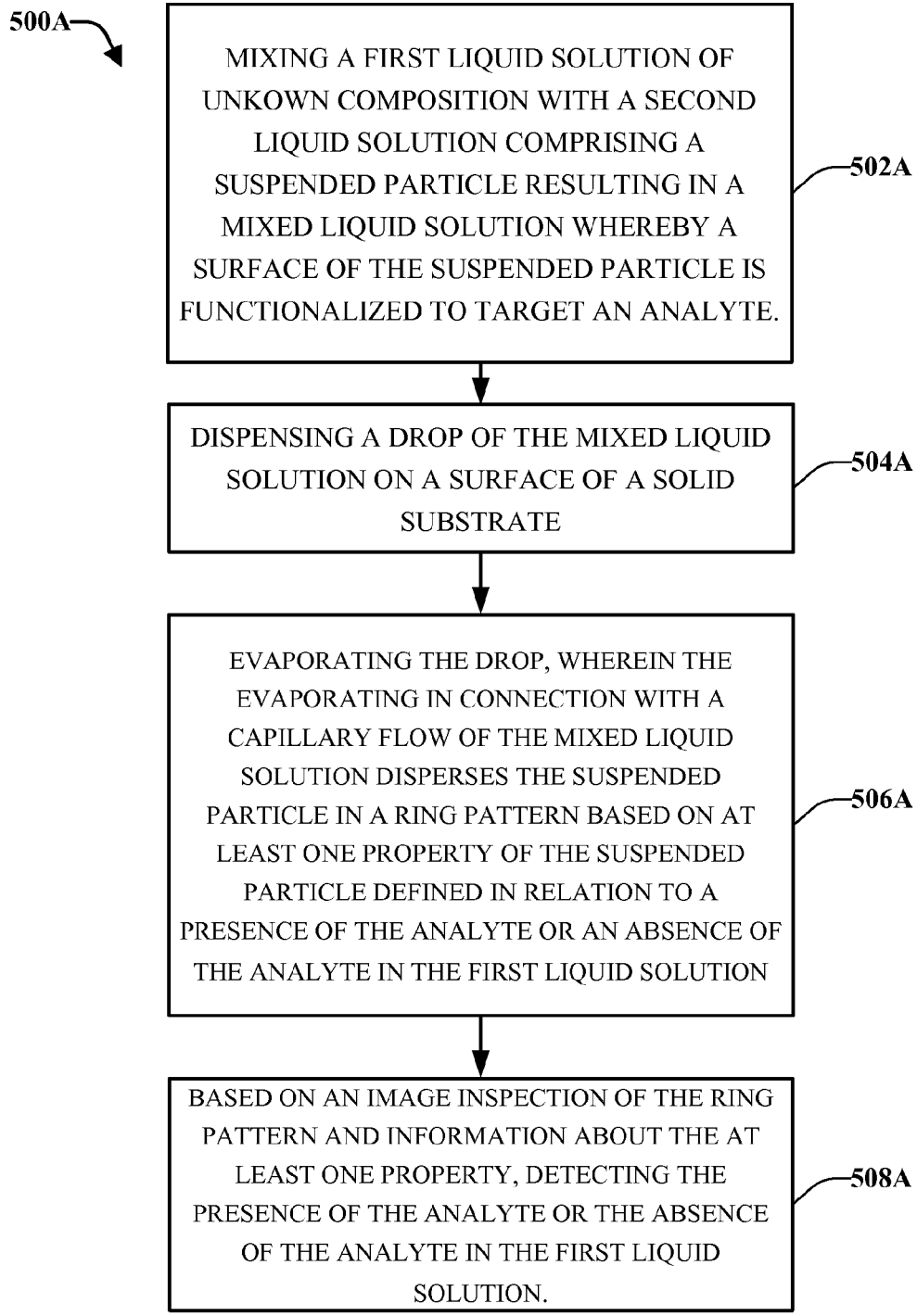
FIG. 5A is an example non-limiting process flow diagram of a method for detecting the presence or absence of an analyte in a liquid solution.
Figure 5B:
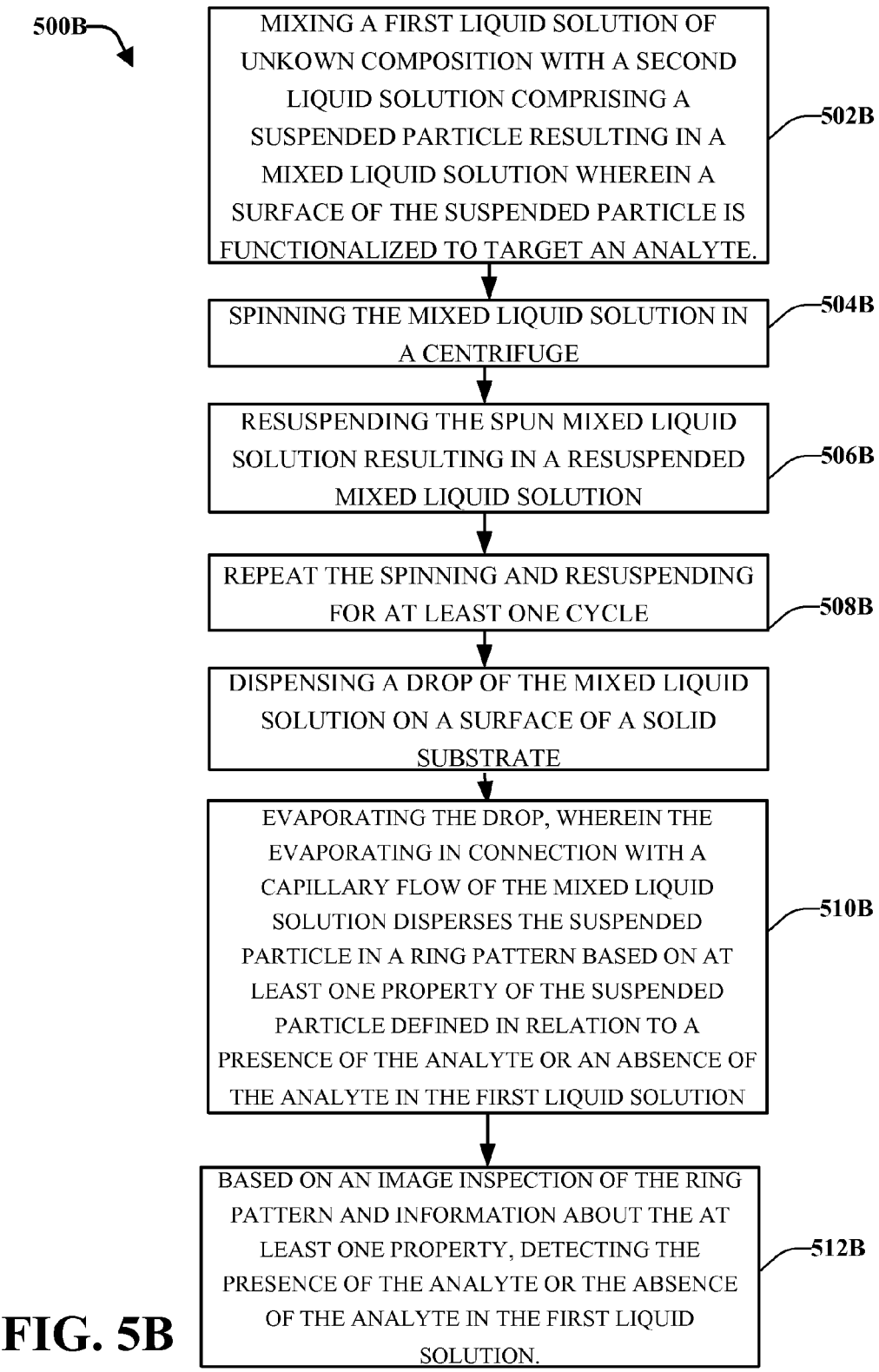
FIG. 5B is an example non-limiting process flow diagram of a method for detecting the presence or absence of an analyte in a liquid solution.

Turning now to FIG. 4, illustrated is an example non-limiting schematic block diagram of device 400. In an aspect, device 400 comprises a mixing portion 110 configured to receive and mix a first liquid solution 102 and a second liquid 406 comprising a microsphere 408 coupled to a detection agent, thereby resulting in a mixed liquid 412 in the mixing portion 110. In an aspect, device 400 employs a surface of a non-porous material 410 configured to receive and allow evaporation of a drop 414 of the mixed liquid 412 from the surface of the non-porous material 410. Furthermore, in an aspect, device 400 comprises a processing device 130 configured to analyze image data, received from an imaging element and representing a ring pattern 416 that remains after the drop has evaporated from the surface, to determine a presence or an absence of a target substance in the first liquid based on the image data.

In an aspect, a mixing portion 110 can be configured to receive and mix a first liquid solution 102 and a second liquid 406 comprising a microsphere 408 coupled to a detection agent. The first liquid solution 102 can be of unknown composition and further device 400 can detect an analyte 104 of interest within first liquid solution 102. In an aspect, second liquid 406 can comprise one or more microsphere wherein each respective microsphere can be of uniform or differentiated sizes. Each microsphere 408 can possess varying diameters respectively and be comprised of materials such as glass, ceramic, metal, any combination of such materials, or other such materials. As illustrated in FIG. 4, each microsphere 408 can be coupled to a detection agent via a functional group. The functional group can facilitate the microsphere to form a bond or linkage with analyte 104 via a detection agent. In an aspect, the reactive, non-limiting functional groups can be alcohols, amines, carboxylates, anhydrides, vinyls, sulfhydryls, epoxies, aldehydes, or other such molecules.

Furthermore, in an aspect, the detection agent can be an antibody, antigen, protein, protein receptor, drug receptor, drug, peptide receptor, peptide, protein receptor, protein, oligonucleotide, DNA, RNA, enzyme, nucleic acid, polymer, lipid or other non-limiting detection agent. The detection agent can be complimentary to analyte 104 thereby binding with analyte 104 following contact with the detection agent. Thus, contact between detection agent and analyte 104 can be facilitated by mixing first liquid solution 102 with second liquid 406 (e.g., via mixing portion 110). A drop 114 of the mixed liquid 412 can be dispersed onto the surface of non-porous material 410 which can be glass, metal, or any material lacking porosity. In an aspect, drop 114 evaporates and the remaining ring pattern 416 can be analyzed by processing device 130. In an aspect, processing device 130 can be an individual analyzing ring pattern 416 via visual inspection to determine the presence or absence of analyte 104 based on various characteristics (e.g., shape, size, ring formation, etc.) of ring pattern 416. In another aspect, processing device 130 can be a digital device configured to analyze image data (e.g., captured by a camera). The analysis of ring pattern 416, via observation by a person (e.g., technician) or via digital processing can determine the presence or absence of analyte 104.

FIGS. 5-10 illustrate methods and/or flow diagrams in accordance with embodiments of this disclosure. For simplicity of explanation, the methods are depicted and described as a series of acts. However, acts in accordance with this disclosure can occur in various orders and/or concurrently, and with other acts not presented and described in this disclosure. Furthermore, not all illustrated acts may be required to implement the methods in accordance with the disclosed subject matter Referring now to FIG. 5A and FIG. 5B, illustrated are example non-limiting process flow diagrams of a method 500A and a method 500B for detecting an analyte. Method 500A facilitates the creation of patterns that indicate, by inspection of the patterns, the presence or absence of an analyte in a liquid sample.

At element 502A, a first liquid solution of unknown composition can be mixed (e.g., using mixing portion 120) with a second liquid solution comprising a suspended particle resulting in a mixed liquid solution whereby a surface of the suspended particle is functionalized to target an analyte. At element 504A, a drop of the mixed liquid solution is dispensed on a surface of a solid substrate (e.g., using solid substrate surface 120). At element 506A, the drop is evaporated, wherein the evaporation in connection with a capillary flow of the mixed liquid solution disperses the suspended particle in a ring pattern based on at least one property of the suspended particle defined in relation to a presence of the analyte or an absence of the analyte in the first liquid solution. At element 508A, the presence or absence of the analyte in the first liquid solution is detected based on an image inspection (e.g., using processing device 130) of the ring pattern and information about the at least one property.

Method 500B facilitates the creation of patterns that indicate, by inspection of the patterns, the presence or absence of an analyte in a liquid sample. At element 502B, a first liquid solution of unknown composition can be mixed (e.g., using mixing portion 120) with a second liquid solution comprising a suspended particle resulting in a mixed liquid solution whereby a surface of the suspended particle is functionalized to target an analyte. At element 504B, the mixed liquid solution is spun in a centrifuge. At element 506B, the spun mixed liquid solution is resuspended. The element 504B and element 506B are conducted for at least one cycle. At element 508B, a drop of the mixed liquid solution is dispensed on a surface of a solid substrate (e.g., using solid substrate surface 120). At element 510B, the drop is evaporated, wherein the evaporation in connection with a capillary flow of the mixed liquid solution disperses the suspended particle in a ring pattern based on at least one property of the suspended particle defined in relation to a presence of the analyte or an absence of the analyte in the first liquid solution. At element 512B, the presence or absence of the analyte in the first liquid solution is detected based on an image inspection (e.g., using processing device 130) of the ring pattern and information about the at least one property.

Figure 6:
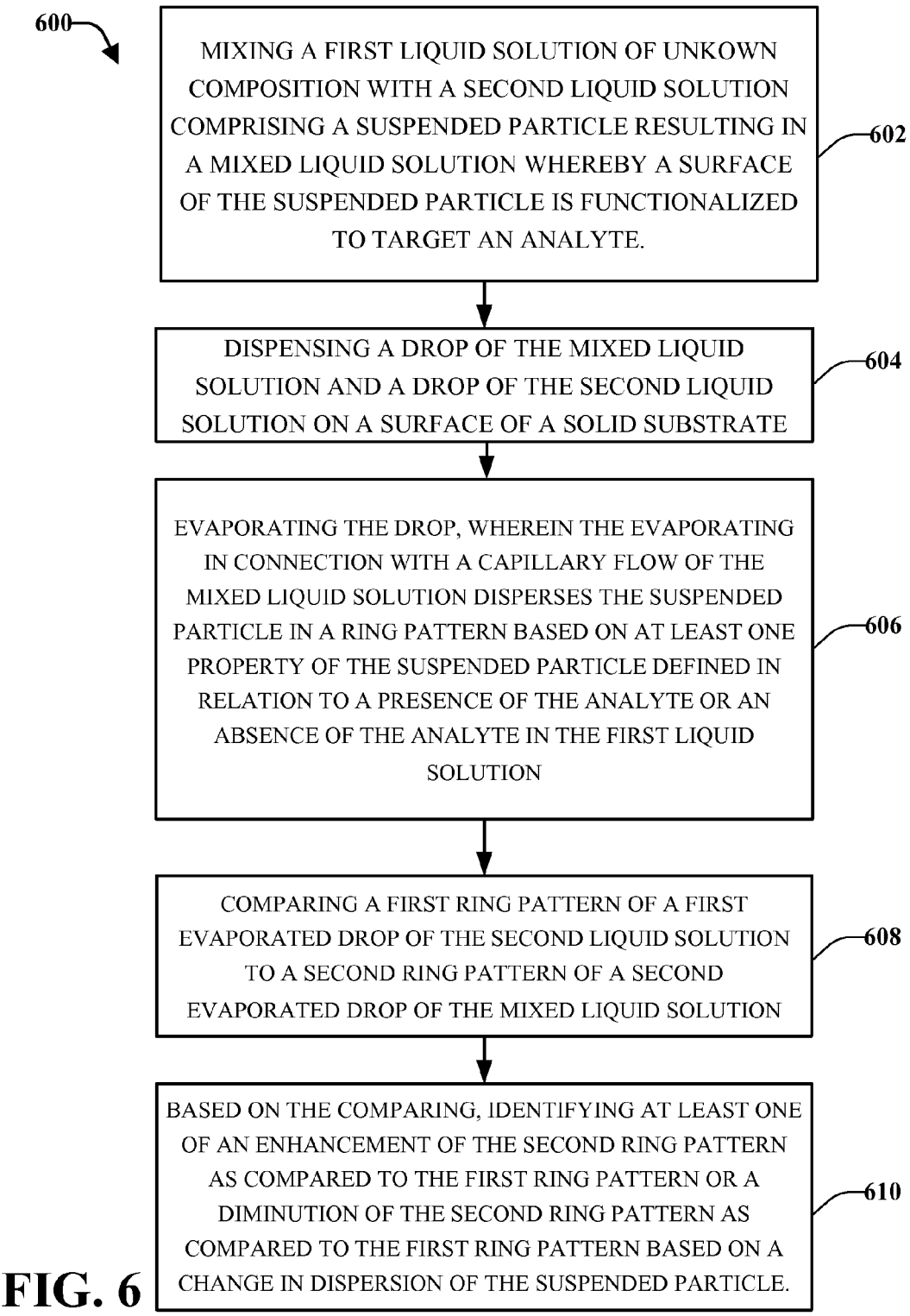
FIG. 6 is an example non-limiting process flow diagram of a method for detecting the presence or absence of an analyte in a liquid solution by comparing a first ring pattern to a second ring pattern.

Referring now to FIG. 6, illustrated is an example non-limiting process flow diagram of a method 600 for detecting an analyte. Method 600 facilitates the creation of patterns that indicate, via inspection of the patterns, the presence or absence of an analyte in a liquid sample.

At element 602, a first liquid solution of unknown composition is mixed (e.g., using mixing portion 110) with a second liquid solution comprising a suspended particle resulting in a mixed liquid solution whereby a surface of the suspended particle is functionalized to target an analyte. At element 604, a drop of the mixed liquid solution and a drop of the second liquid solution is dispensed on a surface of a solid substrate (e.g., using solid substrate surface 120). At element 606, the drop is evaporated wherein the evaporating in connection with a capillary flow of the mixed liquid solution disperses the suspended particle in a ring pattern based on at least one property of the suspended particle defined in relation to a presence of the analyte or an absence of the analyte in the first liquid solution. At element 608, a first ring pattern of a first evaporated drop of the second liquid solution is compared to a second ring pattern of a second evaporated drop of the mixed liquid solution. At element 610, at least one of an enhancement or diminution of the second ring pattern is identified (e.g., using processing device 130) as compared to the first ring pattern based on a change in dispersion of the suspended particle.

Figure 7:
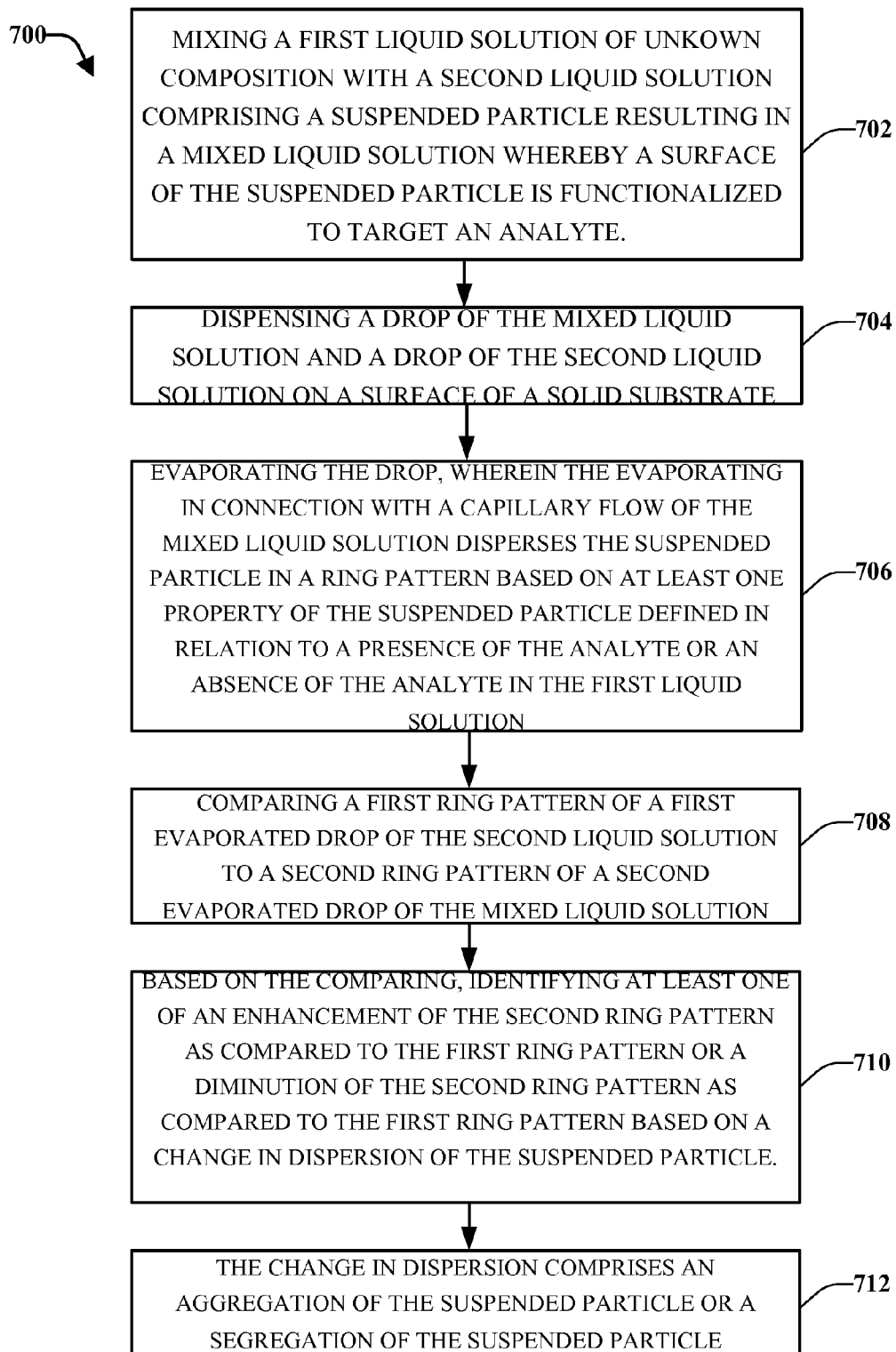
FIG. 7 is an example non-limiting process flow diagram of a method for detecting the presence or absence of an analyte in a liquid solution by comparing a first ring pattern to a second ring pattern.

Referring now to FIG. 7, illustrated is an example non-limiting process flow diagram of a method 700 for detecting an analyte. Method 700 facilitates the creation of patterns that indicate, via inspection of the patterns, the presence or absence of an analyte in a liquid sample.

At element 702, a first liquid solution of unknown composition is mixed (e.g., using mixing portion 110) with a second liquid solution comprising a suspended particle resulting in a mixed liquid solution whereby a surface of the suspended particle is functionalized to target an analyte. At element 704, a drop of the mixed liquid solution and a drop of the second liquid solution is dispensed on a surface of a solid substrate (e.g., using solid substrate surface 120). At element 706, the drop is evaporated wherein the evaporating in connection with a capillary flow of the mixed liquid solution disperses the suspended particle in a ring pattern based on at least one property of the suspended particle defined in relation to a presence of the analyte or an absence of the analyte in the first liquid solution. At element 708, a first ring pattern of a first evaporated drop of the second liquid solution is compared to a second ring pattern of a second evaporated drop of the mixed liquid solution. At element 710, at least one of an enhancement or diminution of the second ring pattern is identified (e.g., using processing device 130) as compared to the first ring pattern based on a change in dispersion of the suspended particle. At element 712, the change in dispersion comprises an aggregation of the suspended particle or a segregation of the suspended particle.

Figure 8:
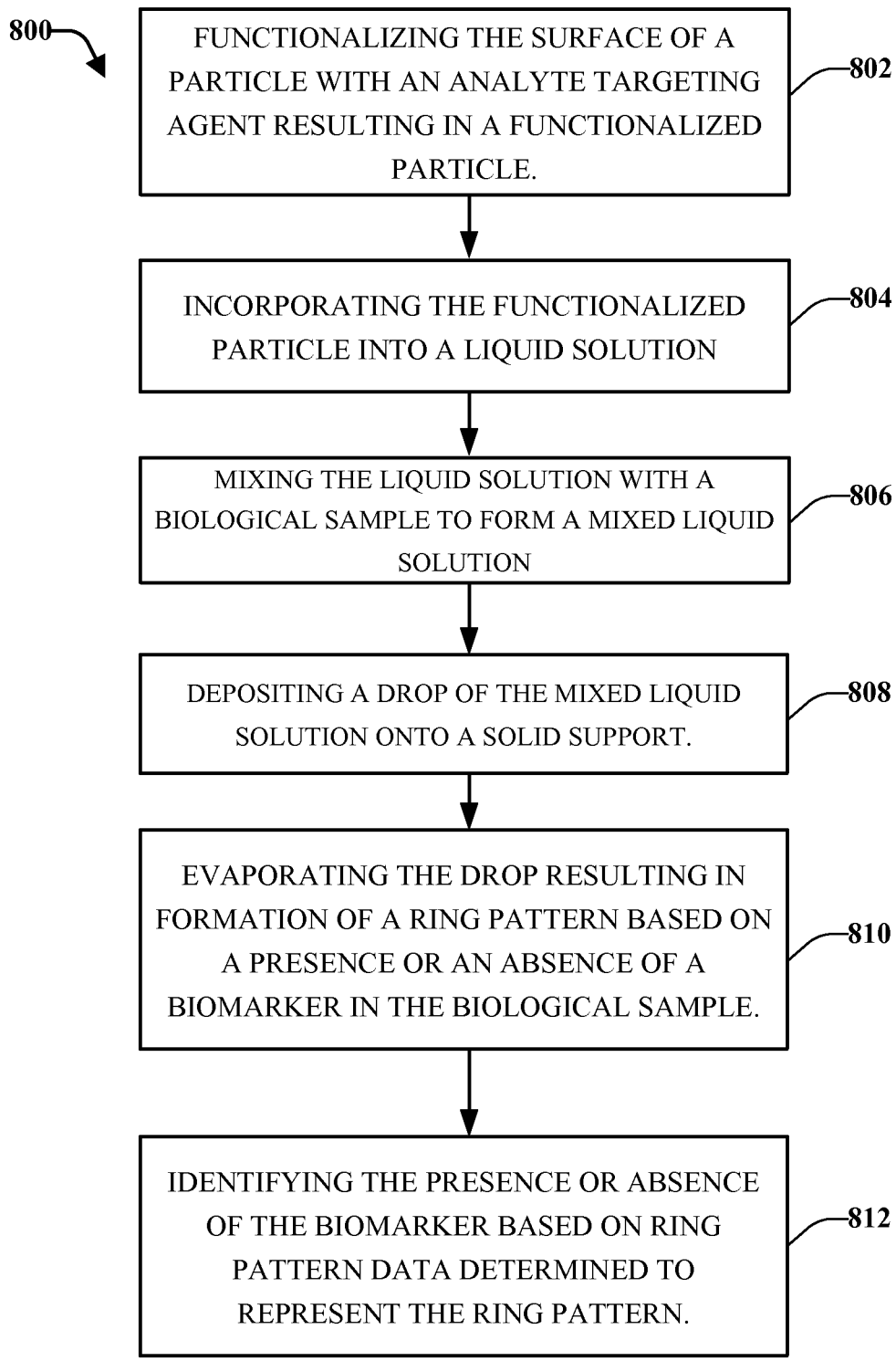
FIG. 8 is an example non-limiting process flow diagram of a method for detecting the presence or absence of an analyte in a liquid solution.

Referring now to FIG. 8, illustrated is an example non-limiting process flow diagram of a method 800 for detecting an analyte. Method 800 facilitates the creation of patterns that indicate, via inspection of the patterns, the presence or absence of an analyte in a liquid sample.

At element 802, the surface of a particle is functionalized with an analyte-targeting agent resulting in a functionalized particle. At element 804, the functionalized particle is incorporated into a liquid solution. At element 806, the liquid solution is mixed (e.g., using mixing component 110) with a biological sample to form a mixed liquid solution. At, element 808, a drop of the mixed liquid solution is deposited onto a solid support (e.g., using solid substrate surface 120). At element 810, the drop is evaporated resulting in formation of a ring pattern based on a presence or an absence of a biomarker in the biological sample. At element 812, the presence or absence of the biomarker is identified (e.g., using processing device 130) based on ring pattern data determined to represent the ring pattern.

Figure 9:
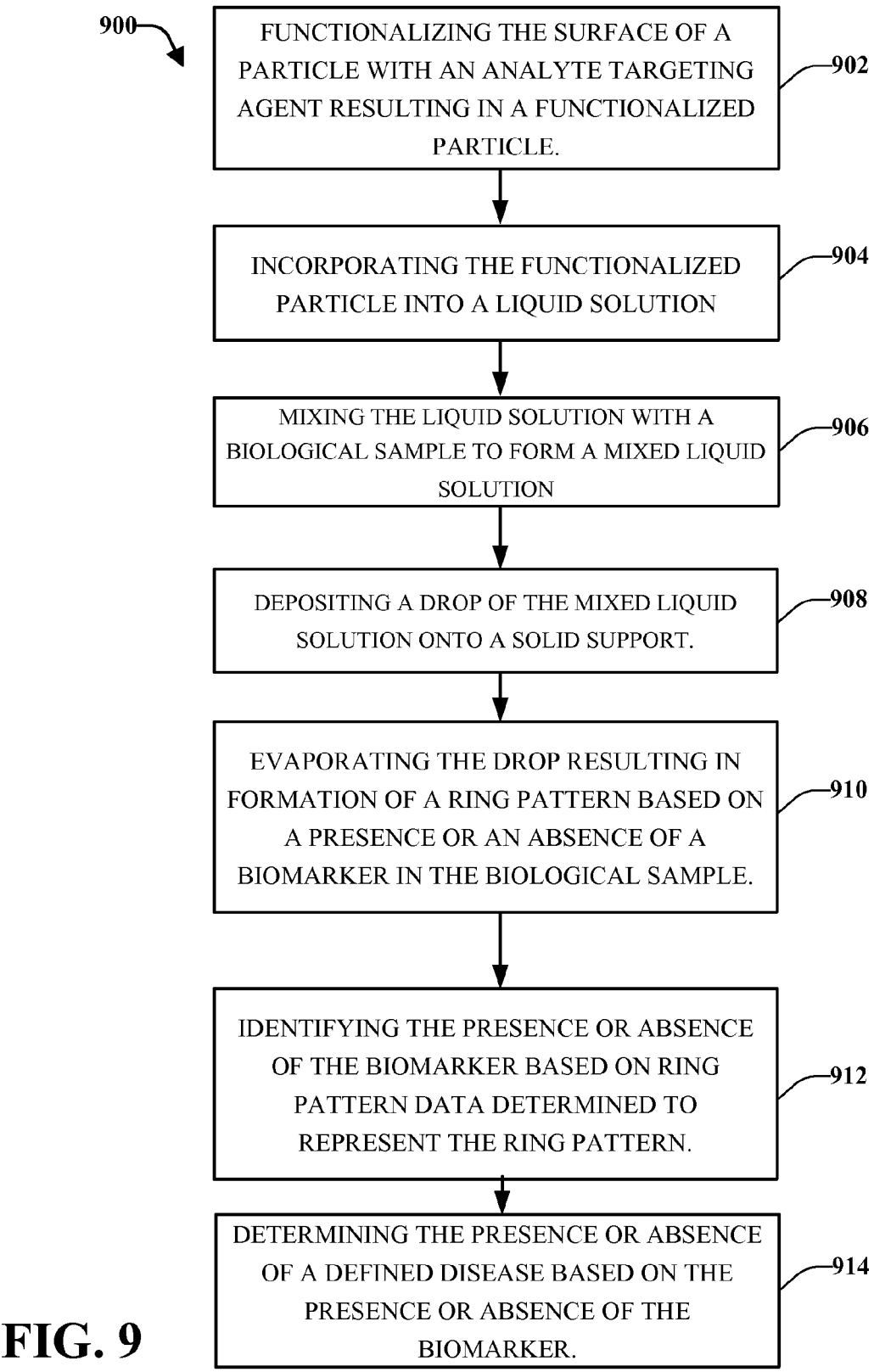
FIG. 9 is an example non-limiting process flow diagram of a method for detecting the presence or absence of an analyte in a liquid solution.

Referring now to FIG. 9, illustrated is an example non-limiting process flow diagram of a method 900 for detecting an analyte. Method 900 facilitates the creation of patterns that indicate, via inspection of the patterns, the presence or absence of an analyte in a liquid sample.

At element 902, the surface of a particle is functionalized with an analyte-targeting agent resulting in a functionalized particle. At element 904, the functionalized particle is incorporated into a liquid solution. At element 906, the liquid solution is mixed (e.g., using mixing component 110) with a biological sample to form a mixed liquid solution. At, element 908, a drop of the mixed liquid solution is deposited onto a solid support (e.g., using solid substrate surface 120). At element 910, the drop is evaporated resulting in formation of a ring pattern based on a presence or an absence of a biomarker in the biological sample. At element 912, the presence or absence of the biomarker is identified (e.g., using processing device 130) based on ring pattern data determined to represent the ring pattern. At element 914, the presence or absence of a defined disease is determined based on the presence or absence of the biomarker.

Figure 10:
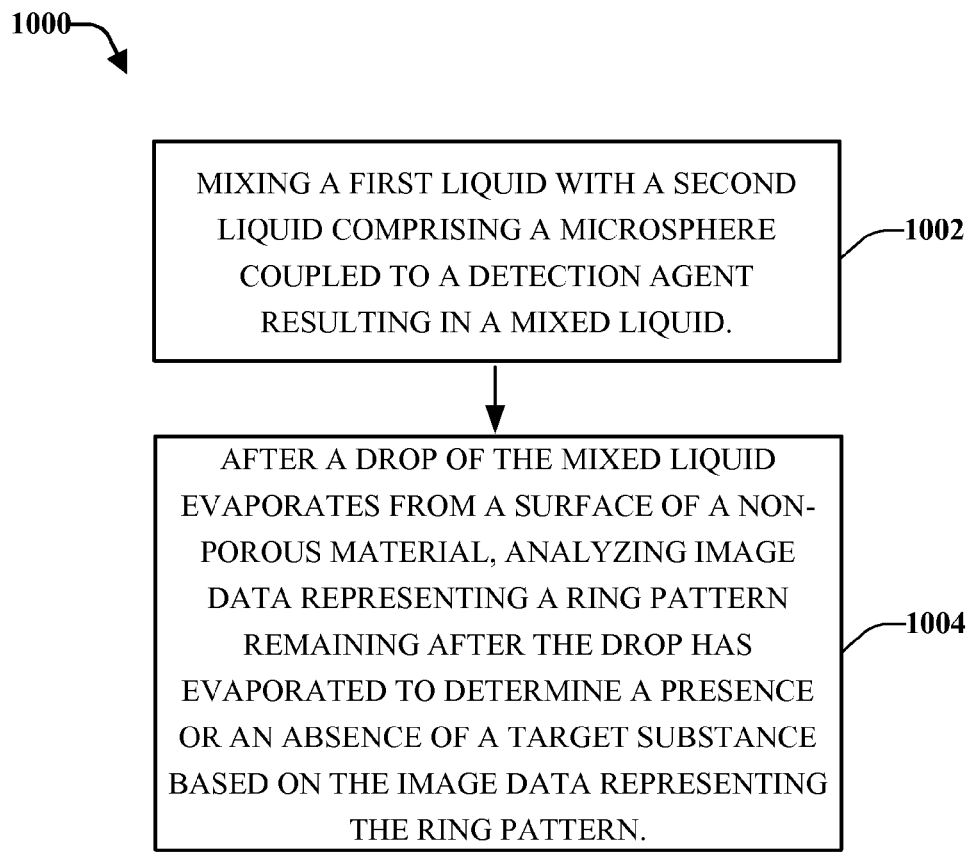
FIG. 10 is an example non-limiting process flow diagram of a method for detecting the presence or absence of an analyte in a liquid solution.

Referring now to FIG. 10, illustrated is an example non-limiting process flow diagram of a method 1000 for detecting an analyte. Method 1000 facilitates the creation of patterns that indicate, via inspection of the patterns, the presence or absence of an analyte in a liquid sample.

At element 1002, a first liquid is mixed (e.g., using mixing component 110) with a second liquid comprising a microsphere coupled to a detection agent resulting in a mixed liquid. At element 1004, image data representing a ring pattern remaining after a drop of the mixed liquid evaporates from a surface of a non-porous material is analyzed to determine a presence or an absence of a target substance based on the image data representing the ring pattern.

What has been described above includes examples of the embodiments of the subject disclosure. It is, of course, not possible to describe every conceivable combination of components or methods for purposes of describing the claimed subject matter, but it is to be appreciated that many further combinations and permutations of the various embodiments are possible. Accordingly, the claimed subject matter is intended to embrace all such alterations, modifications, and variations that fall within the spirit and scope of the appended claims. While specific embodiments and examples are described in this disclosure for illustrative purposes, various modifications are possible that are considered within the scope of such embodiments and examples, as those skilled in the relevant art can recognize.

In addition, the words "example" or "exemplary" is used herein to mean serving as an example, instance, or illustration. Any aspect or design described herein as "exemplary" is not necessarily to be construed as preferred or advantageous over other aspects or designs. Rather, use of the word exemplary is intended to present concepts in a concrete fashion. As used in this application, the term "or" is intended to mean an inclusive "or" rather than an exclusive "or". That is, unless specified otherwise, or clear from context, "X employs A or B" is intended to mean any of the natural inclusive permutations. That is, if X employs A; X employs B; or X employs both A and B, then "X employs A or B" is satisfied under any of the foregoing instances. In addition, the articles "a" and "an" as used in this application and the appended claims should generally be construed to mean "one or more" unless specified otherwise or clear from context to be directed to a singular form.

In addition, while an aspect may have been disclosed with respect to only one of several embodiments, such feature may be combined with one or more other features of the other embodiments as may be desired and advantageous for any given or particular application. Furthermore, to the extent that the terms "includes," "including," "has," "contains," variants thereof, and other similar words are used in either the detailed description or the claims, these terms are intended to be inclusive in a manner similar to the term "comprising" as an open transition word without precluding any additional or other elements. Numerical data, such as temperatures, concentrations, times, ratios, and the like, are presented herein in a range format. The range format is used merely for convenience and brevity. The range format is meant to be interpreted flexibly to include not only the numerical values explicitly recited as the limits of the range, but also to include all the individual numerical values or sub-ranges encompassed within the range as if each numerical value and sub-range is explicitly recited. When reported herein, any numerical values are meant to implicitly include the term "about." Values resulting from experimental error that can occur when taking measurements are meant to be included in the numerical values.

What is claimed is:

1. A device, comprising:
   a mixing portion configured to receive and mix a first liquid solution of unknown composition with a second liquid solution comprising a first non-magnetic suspended particle and a second non-magnetic suspended particle resulting in a mixed liquid solution, wherein a first surface of the first non-magnetic suspended particle and a second surface of the second non-magnetic suspended particle are functionalized to target an analyte, wherein the first non-magnetic suspended particle is a non-spherical particle and wherein the second non-magnetic suspended particle is a different size and a different shape from the first non-magnetic suspended particle;
   a surface of a solid substrate configured to receive and evaporate a drop of the mixed liquid solution, wherein evaporation of the drop in connection with an altered resistance to capillary flow of the mixed liquid solution disperses the first non-magnetic suspended particle and the second non-magnetic suspended particle in a ring pattern based on at least one property of the first non-magnetic suspended particle and the second non-magnetic suspended particle defined in relation to a presence of the analyte or an absence of the analyte in the first liquid solution; and
   a processing device configured to inspect image data representing ring pattern information associated with the ring pattern, and detect the presence of the analyte or the absence of the analyte in the first liquid solution based on at least one property of the ring pattern information, wherein the different size and the different shape of the first non-magnetic suspended particle and the second non-magnetic suspended particle in the second liquid solution create the altered resistance to capillary flow after the first non-magnetic suspended particle and the second non-magnetic suspended particle segregate apart or aggregate together as a result of the presence or the absence of the analyte in the first liquid solution.

2. The device of claim 1, wherein the analyte is at least one of a nucleic acid, a protein, an ion or a chemical compound.

3. The device of claim 2, wherein the protein is a Botulinum toxin.

4. The device of claim 2, wherein the ion is a metal ion.

5. A device, comprising:
   a mixing portion configured to receive and mix a first liquid and a second liquid comprising a non-magnetic microsphere particle coupled to a first detection agent and a non-magnetic non-spherical particle coupled to a second detection agent, thereby resulting in a mixed liquid in the mixing portion, wherein the non-magnetic microsphere particle and the non-magnetic non-spherical particle differ in size and shape respectively;
   a surface of a non-porous material configured to receive and allow evaporation of a drop in connection with an altered resistance to capillary flow of the mixed liquid from the surface of the non-porous material; and
   a processing device configured to analyze image data representing a ring pattern that remains after the drop has evaporated from the surface, to determine a presence or an absence of a target substance in the first liquid based on the image data, wherein a difference in the size and the shape of the non-magnetic microsphere particle and the non-magnetic non-spherical particle creates the altered resistance to capillary flow after the non-magnetic microsphere particle and the non-magnetic non-spherical particle segregate apart or aggregate together based on the presence or the absence of the target substance in the first liquid.

6. The device of claim 5, wherein the target substance is at least one of a nucleic acid, a protein, an ion or a chemical compound.

7. The device of claim 6, wherein the ion is a metal ion.

8. The device of claim 6, wherein the protein is a Botulinum toxin.

9. A device, comprising:
   a mixing portion configured to receive and mix a first liquid solution and a second liquid solution comprising a non-magnetic suspended spherical particle and a non-magnetic suspended non-spherical particle resulting in a mixed liquid solution, wherein a surface of the non-magnetic suspended spherical particle and the non-magnetic suspended non-spherical particle are functionalized to target an analyte within the first liquid solution, and wherein the non-magnetic suspended spherical particle and the non-magnetic suspended non-spherical particle differ in size and shape respectively;
   a surface of a solid substrate configured to receive and allow evaporation of a first drop in connection with an altered resistance to capillary flow of the mixed liquid solution and a second drop of the second liquid solution;
   a first processing device configured to analyze image data representing first ring pattern information remaining after evaporation of the first drop and second ring pattern information remaining after evaporation of the second drop; and
   a second processing device configured to detect at least one of an enhancement of the first ring pattern information as compared to the second ring pattern information or a diminution of the first ring pattern information as compared to the second ring pattern information based on a change in dispersion of the non-magnetic suspended spherical particle and non-magnetic suspended non-spherical particle to determine a presence or an absence of the analyte based on the image data, wherein a difference in the size and shape between the non-magnetic suspended spherical particle and the non-magnetic suspended non-spherical particle creates the altered resistance to capillary flow after the non-magnetic suspended spherical particle and the non-magnetic suspended non-spherical particle segregate apart or aggregate together based on the presence or absence of the analyte within the first liquid solution.

10. The device of claim 9, wherein the change in dispersion comprises an aggregation of the non-magnetic suspended spherical particle and the non-magnetic suspended non-spherical particle or a segregation of the non-magnetic suspended spherical particle and the non-magnetic suspended non-spherical particle.

11. The device of claim 10, wherein the aggregation or the segregation is based on a first shape of the non-magnetic suspended non-spherical particle, a first size of the non-magnetic suspended non-spherical particle, an enhancement of an inter-particle force between the non-magnetic suspended spherical particle and the non-magnetic suspended non-spherical particle, or a reduction of the inter-particle force between the non-magnetic suspended spherical particle and the non-magnetic suspended non-spherical particle.

12. A method, comprising:
mixing a first liquid solution of unknown composition with a second liquid solution comprising a set of non-magnetic suspended particles resulting in a mixed liquid solution whereby a surface of the set of non-magnetic suspended particles is functionalized to target an analyte, wherein the set of non-magnetic suspended particles comprises a first subset of non-magnetic suspended particles and a second subset of non-magnetic suspended particles, wherein the first subset of non-magnetic suspended particles comprises a first size and a first shape, and wherein the second subset of non-magnetic suspended particles comprises a second size and a second shape that are different from the first size and the first shape;
dispensing a drop of the mixed liquid solution on a surface of a solid substrate;
evaporating the drop, wherein the evaporating in connection with an altered resistance to capillary flow of the mixed liquid solution disperses the set of non-magnetic suspended particles in a ring pattern based on at least one property of the set of non-magnetic suspended particles defined in relation to a presence of the analyte or an absence of the analyte in the first liquid solution; and
based on an image inspection of the ring pattern and information corresponding to the at least one property, detecting the presence of the analyte or the absence of the analyte in the first liquid solution, wherein a difference between the first size, the first shape, the second size, and the second shape of the first subset of non-magnetic suspended particles and the second subset of non-magnetic suspended particles respectively creates the altered resistance to capillary flow after the set of non-magnetic suspended particles segregates apart or aggregates together as a result of the presence or the absence of the analyte in the first liquid solution.

13. The method of claim 12, wherein the analyte is at least one of a nucleic acid, a protein, an ion, or a chemical compound.

14. The method of claim 13, wherein the ion is a metal ion.

15. The method of claim 13, wherein the protein is a Botulinum toxin.

16. The method of claim 12, wherein the first subset of non-magnetic suspended particles are spherical particles and the second subset of non-magnetic suspended particles are non-spherical particles.

17. The method of claim 16, wherein the spherical particles can flow to the edge of the drop in accordance with the capillary flow and accumulate at the point of contact between the surface of the solid substrate and edges of the drop thereby creating a ring pattern.

18. The method of claim 12, wherein the first subset of non-magnetic suspended particles is ellipsoid particles, spherical particle aggregates or non-spherical particle aggregates that resist the capillary flow of the mixed liquid solution and decrease or stop formation of the ring pattern.

19. The method of claim 12, further comprising:
comparing a first ring pattern of a first evaporated drop of the second liquid solution to a second ring pattern of a second evaporated drop of the mixed liquid solution; and
based on the comparing, identifying at least one of an enhancement of the second ring pattern as compared to the first ring pattern or a diminution of the second ring pattern as compared to the first ring pattern based on a change in dispersion of the set of non-magnetic suspended particles.

20. The method of claim 19, wherein the change in dispersion comprises an aggregation of the set of non-magnetic suspended particles or a segregation of the set of non-magnetic suspended particles.

21. The method of claim 20, wherein the aggregation or the segregation is based on a shape of the set of non-magnetic suspended particles, a size of the set of non-magnetic suspended particles, an enhancement of an inter-particle force between two or more suspended particles of the set of non-magnetic suspended particles, or a reduction of the inter-particle force between the two or more of the set of non-magnetic suspended particles.

22. The method of claim 21, wherein the enhancement of the inter-particle force or the reduction of the inter-particle force is based on DNA hybridization, RNA hybridization, absorption of a protein by the set of non-magnetic suspended particles, an affinity to an immune system analyte by the set of non-magnetic suspended particles, or a change in a surface charge of the set of non-magnetic suspended particles.

23. The method of claim 12, wherein the second liquid solution comprises a first suspended particle of the second subset of non-magnetic suspended particles and a second suspended particle of the first subset of non-magnetic suspended particles.

24. The method of claim 23, wherein the first suspended particle is a spherical particle and the second suspended particle is a non-spherical particle.

25. A method, comprising:
functionalizing a surface of a set of non-magnetic particles with an analyte targeting agent resulting in a set of non-magnetic functionalized particles, wherein the set of non-magnetic functionalized particles comprises spherical particles and non-spherical particles of varying sizes;
incorporating the set of non-magnetic functionalized particles into a liquid solution;
mixing the liquid solution with a biological sample to form a mixed liquid solution;
depositing a drop of the mixed liquid solution onto a solid support;
evaporating the drop in connection with an altered resistance to capillary flow resulting in formation of a ring pattern based on a presence or an absence of a biomarker in the biological sample; and
identifying the presence or the absence of the biomarker based on ring pattern data determined to represent the ring pattern, wherein a difference in shape and size between the spherical particles and the non-spherical particles creates the altered resistance to capillary flow after the set of non-magnetic functionalized particles segregates apart or aggregates together as a result of the presence or the absence of the biomarker in the biological sample.

26. The method of claim 25, wherein the biomarker comprises at least one of an mRNA structure, an oligonucleotide structure, or a protein structure.

27. The method of claim 25, wherein the biological sample comprises saliva.

28. The method of claim 25, further comprising determining the presence or absence of a defined disease based on the presence or the absence of the biomarker.

29. The method of claim 28, wherein the defined disease is oral cancer.

30. The method of claim 28, wherein the defined disease is malaria and the biomarker is a protein comprising at least a defined amount of a parasite P. falciparum histidine.

31. A method, comprising:
mixing a first liquid with a second liquid comprising a non-magnetic micro sphere and a non-magnetic ellipsoid coupled to a detection agent resulting in a mixed liquid, wherein the non-magnetic microsphere comprises a first size and the non-magnetic ellipsoid comprises a second size that is different from the first size;
adding a drop of the mixed liquid to a surface of a non-porous material;
evaporating the drop of the mixed liquid from the surface of the non-porous material; and
after a drop of the mixed liquid evaporates from a surface of a non-porous material in connection with an altered resistance to capillary flow, analyzing image data representing a ring pattern remaining after the drop has evaporated to determine a presence or an absence of a target substance in the first liquid based on the image data representing the ring pattern, wherein a first difference between the first size and second size and a second difference between a spherical shape of the non-magnetic microsphere and a non-spherical shape of the non-magnetic ellipsoid create the altered resistance to capillary flow after the non-magnetic microsphere and the non-magnetic ellipsoid segregate apart or aggregate together as a result of the presence or the absence of the target substance in the first liquid.

32. The method of claim 31, wherein the detection agent is an aptamer.

33. The method of claim 31, wherein the target substance is a metal ion or a Botulinum toxin.

34. A method, comprising:
mixing a first liquid solution of unknown composition with a second liquid solution comprising a set of non-magnetic suspended particles resulting in a mixed liquid solution wherein a surface of the set of non-magnetic suspended particles is functionalized to target an analyte, wherein the set of non-magnetic suspended particles comprises a first subset of particles comprising a first size and a first shape and a second subset of particles comprising a second size and a second shape that is different from the first size and the first shape;
spinning the mixed liquid solution in a centrifuge;
resuspending the spun mixed liquid solution resulting in a resuspended mixed liquid solution;
repeating the spinning and resuspending for at least one cycle;
dispensing a drop of the resuspended mixed liquid solution on a surface of a solid substrate;
evaporating the drop, wherein the evaporating in connection with an altered resistance to capillary flow of the mixed liquid solution disperses the set of non-magnetic suspended particles in a ring pattern based on at least one property of the set of non-magnetic suspended particles defined in relation to a presence of the analyte or an absence of the analyte in the first liquid solution; and
based on an image inspection of the ring pattern and information about the at least one property, detecting the presence of the analyte or the absence of the analyte in the first liquid solution, wherein a first difference between the first size and the second size and a second difference between the first shape and the second shape creates the altered resistance to capillary flow after the set of non-magnetic suspended particles segregates apart or aggregates together based on the presence or the absence of the analyte in the first liquid solution.

35. The method of claim 34, further comprising comparing the ring pattern to a second ring pattern of a second evaporated drop of the second liquid solution; and
based on the comparing, identifying at least one of an enhancement of the ring pattern as compared to the second ring pattern or a diminution of the ring pattern as compared to the second ring pattern based on a change in dispersion of the set of non-magnetic suspended particles.

* * * * *